US011884963B2

(12) United States Patent
Farmer et al.

(10) Patent No.: US 11,884,963 B2
(45) Date of Patent: *Jan. 30, 2024

(54) METHODS OF DEPLETING A TARGET MOLECULE FROM AN INITIAL COLLECTION OF NUCLEIC ACIDS, AND COMPOSITIONS AND KITS FOR PRACTICING THE SAME

(71) Applicant: Takara Bio USA, Inc., Mountain View, CA (US)

(72) Inventors: Andrew Alan Farmer, Los Altos, CA (US); Craig Betts, Mountain View, CA (US); Nathalie Bolduc, Castro Valley, CA (US)

(73) Assignee: Takara Bio USA, Inc., San Jose, CA (US)

( * ) Notice: Subject to any disclaimer, the term of this patent is extended or adjusted under 35 U.S.C. 154(b) by 186 days.

This patent is subject to a terminal disclaimer.

(21) Appl. No.: 17/235,702

(22) Filed: Apr. 20, 2021

(65) Prior Publication Data

US 2021/0238655 A1    Aug. 5, 2021

Related U.S. Application Data

(63) Continuation of application No. 16/154,414, filed on Oct. 8, 2018, now Pat. No. 10,988,796, which is a continuation of application No. 14/582,081, filed on Dec. 23, 2014, now Pat. No. 10,150,985.

(60) Provisional application No. 61/939,658, filed on Feb. 13, 2014, provisional application No. 62/040,804, filed on Aug. 22, 2014.

(51) Int. Cl.
    C12Q 1/68     (2018.01)
    *C12Q 1/6806*  (2018.01)
    *C12N 15/10*   (2006.01)

(52) U.S. Cl.
     CPC ....... *C12Q 1/6806* (2013.01); *C12N 15/1003* (2013.01)

(58) Field of Classification Search
     USPC .......... 435/6.1, 6.11, 6.12, 91.1, 91.2, 91.51, 435/183; 436/94, 501; 536/23.1, 24.3, 536/24.33
     See application file for complete search history.

(56) References Cited

U.S. PATENT DOCUMENTS

| | | |
|---|---|---|
| 6,759,226 B1 | 7/2004 | Ma et al. |
| 7,919,277 B2 | 4/2011 | Russell et al. |
| 8,361,725 B2 | 1/2013 | Russell et al. |
| 8,546,553 B2 | 10/2013 | Terns et al. |
| 10,150,985 B2 | 12/2018 | Farmer et al. |
| 10,604,802 B2 | 3/2020 | Brown et al. |
| 10,988,796 B2 * | 4/2021 | Farmer ............... C12N 15/1003 |
| 2003/0232410 A1 | 12/2003 | Liljedahl et al. |
| 2004/0018604 A1 | 1/2004 | Hill et al. |
| 2005/0208489 A1 | 9/2005 | Carroll et al. |
| 2006/0063231 A1 | 3/2006 | Li et al. |
| 2006/0188987 A1 | 8/2006 | Guschin et al. |
| 2010/0076057 A1 | 3/2010 | Sontheimer et al. |
| 2010/0093617 A1 | 4/2010 | Barrangou et al. |
| 2011/0111409 A1 | 5/2011 | Sinicropi et al. |
| 2011/0217739 A1 | 9/2011 | Terns et al. |
| 2011/0301073 A1 | 12/2011 | Gregory et al. |
| 2012/0252009 A1 | 10/2012 | Feehery et al. |
| 2013/0158245 A1 | 6/2013 | Russell et al. |
| 2013/0267577 A1 | 10/2013 | Unger |
| 2014/0357523 A1 | 12/2014 | Zeiner et al. |
| 2016/0017396 A1 | 1/2016 | Cann et al. |
| 2016/0053304 A1 | 2/2016 | Wurtzel et al. |
| 2017/0191123 A1 | 7/2017 | Kim et al. |
| 2020/0181700 A1 | 6/2020 | Brown et al. |

FOREIGN PATENT DOCUMENTS

| | | |
|---|---|---|
| CA | 2938669 | 8/2015 |
| CN | 102124126 A | 7/2011 |
| CN | 103502475 A | 1/2014 |
| EP | 3102722 | 12/2016 |
| EP | 3150718 A1 | 4/2017 |
| EP | 3105325 B1 | 12/2019 |
| JP | 2013178140 A | 9/2013 |
| KR | 10-2014-0064526 A | 5/2014 |
| KR | 20140064526 A | 5/2014 |

(Continued)

OTHER PUBLICATIONS

Gasiunas et al., Cas9-crRNA ribonucleoprotein complex mediates specific DNA cleavage for adaptive immunity in bacteria. PNAS, 109, E2579-E2586, published online on Sep. 4, 2012.
Fujita, Toshitsugu, et al., Efficient isolation of specific genomic regions and identification of associated proteins by engineered DNA-binding molecule-mediated chromatin immunoprecipitation (enChiP) using CRISPR, Biochemical and Biophysical Research Communications 439 (2013) 132-136.
Zhulidov et al., Simple cDNA normalization using kamchatka crab duplex-specific nuclease. Nucleic Acids Research, 32, e37, 2004.
Maden et al., Clones of human ribosomal DNA containing the complete 18 S-rRNA and 28 S-rRNA genes. Biochem. J., 246,519-527, 1987.
Carroll, "Staying on target with CRISPR-Cas", Nature Biotechnology (2013), 31(9):807-809.

(Continued)

*Primary Examiner* — Frank W Lu
(74) *Attorney, Agent, or Firm* — Bret E. Field; Bozicevic, Field & Francis LLP

(57) ABSTRACT

Provided are methods of depleting a target nucleic acid from an initial collection of nucleic acids. Aspects of the methods include contacting the initial collection with a nucleic acid guided nuclease specific for the target nucleic acid in a manner sufficient to deplete the target nucleic acid from the initial collection. Depending on a given application, depletion of a target nucleic acid may vary, e.g., where depleting may include cleaving a target nucleic acid in, or selectively separating a target nucleic acid from, the initial collection of nucleic acids. Also provided are compositions and kits for practicing embodiments of the methods.

20 Claims, 10 Drawing Sheets

Specification includes a Sequence Listing.

(56) References Cited

FOREIGN PATENT DOCUMENTS

| WO | WO2011019993 | 2/2011 |
| WO | WO2013126794 | 8/2013 |
| WO | WO2013130824 | 9/2013 |
| WO | WO2013141680 | 9/2013 |
| WO | WO2013142578 | 9/2013 |
| WO | WO2013169398 | 11/2013 |
| WO | WO2013169802 | 11/2013 |
| WO | WO2013176772 | 11/2013 |
| WO | WO2013191775 | 12/2013 |
| WO | WO2014011237 | 1/2014 |
| WO | WO2014011901 | 1/2014 |
| WO | WO2014018423 | 1/2014 |
| WO | WO2014043143 A1 | 3/2014 |
| WO | WO2014200659 | 12/2014 |
| WO | WO2015089277 | 6/2015 |
| WO | WO2015119941 | 8/2015 |
| WO | WO2015122967 A1 | 8/2015 |
| WO | WO2016028887 | 2/2016 |
| WO | WO2016100955 | 6/2016 |
| WO | WO2017031360 | 2/2017 |

OTHER PUBLICATIONS

Elkayam, et al., "The Structure of Human Argonaute-2 in Complex with miR-20a", Cell (2012), 150(1):100-110.

Hwang, et al., "Efficient genome editing in zebrafish using a CRISPR-Cas system", Nature Biotechnology (2013), 31(3):227-229.

Jiang et al., "RNA-guided editing of bacterial genomes using CRISPR-Cas systems", Nature Biotechnology (2013), 31:233-239.

"Notice of Opposition to European Patent EP3105325", dated Sep. 11, 2020 (20 pages).

Kim et al., "Hybrid restriction enzymes: Zinc finger fusions to Fok I cleavage domain", PNAS (1996), 93(3):1156-1160.

Jinek et al., "A Programmable Dual-RNA-Guided DNA Endonuclease in Adaptive Bacterial Immunity", Science (2012), 337:816-821.

Supplemental materials of Jinek et al., A Programmable Dual-RNA-Guided DNA Endonuclease in Adaptive Bacterial Immunity. Science, 337, 816-821, Aug. 17, 2012.

Wang et al., "Nucleation, propagation and cleavage of target RNAs in Ago silencing complexes", Nature (2009), 461(7265):754-761.

O'Connell et al., "Programmable RNA recognition and cleavage by CRISPR/Cas9", Nature (2014), 516(7530):263-266 (15 pages).

Sampson et al., "A CRISPR/Cas system mediates bacterial innate immune evasion and virulence", Nature (2013), 497:254-257.

Sander et al., "CRISPR-Cas systems for editing, regulating and targeting genomes", Nature Biotechnology (2014), 32:347-355.

Sternberg et al., "DNA interrogation by the CRISPR RNA-guided endonuclease Cas9", Nature (2014), 507(7490):62-67.

Swarts et al., "DNA-guided DNA interference by a prokaryotic Argonaute", Nature (2014), 507:258-261.

Wang et al., "Structure of an argonaute silencing complex with a seed-containing guide DNA and target RNA duplex", Nature (2008), 456(7224):921-926.

Mali, P. et al., "RNA-guided human genome engineering via Cas9", Science, Feb. 15, 2013 (Epub. Jan. 3, 2013), vol. 339, No. 6121, pp. 823-826.

Hsu, P.O. et al., "DNA targeting specificity of RNA-guided Cas9 nucleases", Nature Biotechnology, Sep. 2013 (Epub. Jul. 21, 2013), vol. 31, No. 9, pp. 827-832 (NIH Public Author Manuscript Version internal pp. 1-14).

International Search Report and Written Opinion of PCT/US2014/072293, dated Apr. 27, 2015.

Dolinsek, J., et al., "Depletion of Unwanted Nucleic Acid Templates by Selective Cleavage: LNAzymes, Catalytically Active Oligonucleotides Containing Locked Nucleic Acids, Open a New Window for Detecting Rare Microbial Community Members, Applied and Environmental Microbiology," Mar. 2013, vol. 79, No. 5, pp. 1534-1544.

Gu., W., et al., "Depletion of Abundant Sequences by Hybridization (DASH): using Cas9 to remove unwanted high-abundance species in sequencing libraries and molecular counting applications," Genome Biology, vol. 17, No. 1, Mar. 4, 2016 (13 pages).

Morlan, J.D., et al., "Selective Depletion of rRNA Enables Whole Transcriptome Profiling of Archival Fixed Tissue," PLOS ONE, vol. 7, No. 8, Jan. 1, 2012 (8 pages).

Cong, L., et al., "Multiplex Genome Engineering Using CRISPR/Cas Systems," Science, vol. 339, No. 6121, Jan. 3, 2013 (pp. 819-823) including Supplementary Materials.

Golic, G. Kent, "RNA-Guided Nucleases: A New Era for Engineering the Genomes of Model and Nonmodel Organisms", Genetics, vol. 195, Oct. 2013, pp. 303-308.

Zhou et al., The next-generation sequence technology and application, Protein Cell, Jul. 2010, vol. 1, No. 6, p. 520-536.

Zhao et al., Evaluation of two main RNA-seq approaches for gene quantification in clinical RNA sequencing: polyA+ selection versus rRNA depletion, Scientific Reports, Mar. 2018, vol. 8, No. 4781, p. 1-12.

Mutz et al., Transcriptome analysis using next-generation sequencing, Current Opinion in Biotechnology, Feb. 2013, vol. 24, No. 1, p. 22-30.

Yang et al., CRISPR/Cas9-directed genome editing of cultured cells, Current Protocols in Molecular Biology, Jul. 2014, Supp. 107, Unit 31.1, p. 31.1.1-31.1.17.

Ran et al., Genome engineering using the CRISPR-Cas9 system, Nature Protocols, Oct. 2013, vol. 8, No. 11, p. 2281-2308.

Pattanayak et al., High-throughput profiling of off-target DNA cleavage reveals RNA-programmed Cas9 nuclease specificity, Nature Biotechnology, Sep. 2013, vol. 31, No. 9, p. 839-843.

U.S. Appl. No. 61/939,658, filed Feb. 13, 2014.
U.S. Appl. No. 61/935,827, filed Feb. 4, 2014.
U.S. Appl. No. 62/040,307, filed Aug. 21, 2014.
U.S. Appl. No. 62/040,804, filed Aug. 22, 2014.

Zhulidov et al., A method for the preparation of normalized cDNA libraries enriched with full length sequences, Russian Journal of Bioorganic Chemistry, vol. 31, No. 2, Mar. 2005, p. 170-177.

Carpenter et al., Pulling out the 1%: Whole-genome capture for the targeted enrichment of ancient DNA sequencing libraries, The American Journal of Human Genetics, Nov. 7, 2013, vol. 93, No. 5, p. 852-864.

Green et al., Suicide polymerase endonuclease restriction, a novel technique for enhancing PCR amplification of minor DNA templates, Applied and Environmental Microbiology, vol. 71, No. 8, Aug. 1, 2005, p. 4721-4727.

Adiconis et al., Comparative analysis of RNA sequencing methods for degraded or low-input samples, Nature Methods, vol. 10, No. 7, Jul. 2013, p. 623-629.

Gomaa et al., Programmable removal of bacterial strains by use of genome-targeting CRISPR-Cas systems, MBIO, vol. 5, No. 1, Jan. 28, 2014, p. 1-9.

Gasiunas et al., Cas9-crRNA ribonucleoprotein complex mediates specific DNA cleavage for adaptive immunity in bacteria, PNAS, Sep. 4, 2012, p. E2579-E2586, and Supporting Information, p. 1-8.

Affidavit by Keith Brown, In respect of an Opposition to European Patent No. 3105325 in the name of Takara Bio USA, Inc., Apr. 9, 2021, p. 1-6.

Letter to European Patent Office, Applicant's Response to EPO Communication for European Patent Application No. EP14882441.0, dated Aug. 2, 2018, 9 pages.

Takara Bio USA, Inc., SMARTer Stranded Total RNA-Seq Kit v3—Pico Input Mammalian User Manual, 2020, p. 1-26.

Sambrook et al., Molecular Cloning: A Laboratory Manual, 2nd Edition, 1989, Cold Spring Harbor Laboratory Press, Extract, p. E.10-E.11.

Pandey et al., A CRISPR/Cas9-based enhancement of high-throughput single-cell transcriptomics, bioRxiv: the preprint server for biology, Sep. 7, 2022, p. 1-25, and figures, 26 pages.

* cited by examiner

T7-T1-AcGFP
- GCG GCC TCT AAT ACG ACT CAC TAT AGG G(n13)
- GTGAATCGCATCGAGCTGACgttttagagctagaaatagcaag

T7-T2-AcGFP
- GCG GCC TCT AAT ACG ACT CAC TAT AGG G(n13)
- GGAGCGCACCATCTTCTTCGgttttagagctagaaatagcaag

T7-Rev
- GTA CAA GAA AGC TGG GTC TAG AAA AAA AGC ACC G

+Cas9

A

★ Condition used for library cleavage

A

B

SEQUENCE LISTING

<160> NUMBER OF SEQ ID NOS: 45

<210> SEQ ID NO 1
<211> LENGTH: 20
<212> TYPE: RNA
<213> ORGANISM: Artificial Sequence
<220> FEATURE:
<223> OTHER INFORMATION: synthetic

<400> SEQUENCE: 1
uuaucagauc aaaaccaacc                                               20

<210> SEQ ID NO 2
<211> LENGTH: 20
<212> TYPE: RNA
<213> ORGANISM: Artificial Sequence
<220> FEATURE:
<223> OTHER INFORMATION: synthetic

<400> SEQUENCE: 2
uaaucaagaa cgaaagucgg                                               20

<210> SEQ ID NO 3
<211> LENGTH: 20

```
<212> TYPE: RNA
<213> ORGANISM: Artificial Sequence
<220> FEATURE:
<223> OTHER INFORMATION: synthetic

<400> SEQUENCE: 3
gacaagcaua ugcuacuggc                                               20

<210> SEQ ID NO 4
<211> LENGTH: 20
<212> TYPE: RNA
<213> ORGANISM: Artificial Sequence
<220> FEATURE:
<223> OTHER INFORMATION: synthetic

<400> SEQUENCE: 4
cgguacagug aaacugcgaa                                               20

<210> SEQ ID NO 5
<211> LENGTH: 20
<212> TYPE: RNA
<213> ORGANISM: Artificial Sequence
<220> FEATURE:
<223> OTHER INFORMATION: synthetic

<400> SEQUENCE: 5
ggagaggagc gagcgaccaa                                               20

<210> SEQ ID NO 6
<211> LENGTH: 20
<212> TYPE: RNA
<213> ORGANISM: Artificial Sequence
<220> FEATURE:
<223> OTHER INFORMATION: synthetic

<400> SEQUENCE: 6
uagagcuaau acaugccgac                                               20

<210> SEQ ID NO 7
<211> LENGTH: 20
<212> TYPE: RNA
<213> ORGANISM: Artificial Sequence
<220> FEATURE:
<223> OTHER INFORMATION: synthetic

<400> SEQUENCE: 7
uuaucagauc aaaaccaacc                                               20

<210> SEQ ID NO 8
<211> LENGTH: 20
<212> TYPE: RNA
<213> ORGANISM: Artificial Sequence
<220> FEATURE:
<223> OTHER INFORMATION: synthetic

<400> SEQUENCE: 8
ggggcgggcg ccggcggcuu                                               20

<210> SEQ ID NO 9
<211> LENGTH: 20
<212> TYPE: RNA
<213> ORGANISM: Artificial Sequence
<220> FEATURE:
<223> OTHER INFORMATION: synthetic

<400> SEQUENCE: 9
```

```
cgaucgcacg cccccccgugg                                              20

<210> SEQ ID NO 10
<211> LENGTH: 20
<212> TYPE: RNA
<213> ORGANISM: Artificial Sequence
<220> FEATURE:
<223> OTHER INFORMATION: synthetic

<400> SEQUENCE: 10
gguagucgcc gugccuacca                                              20

<210> SEQ ID NO 11
<211> LENGTH: 20
<212> TYPE: RNA
<213> ORGANISM: Artificial Sequence
<220> FEATURE:
<223> OTHER INFORMATION: synthetic

<400> SEQUENCE: 11
ucaggguucg auuccggaga                                              20

<210> SEQ ID NO 12
<211> LENGTH: 20
<212> TYPE: RNA
<213> ORGANISM: Artificial Sequence
<220> FEATURE:
<223> OTHER INFORMATION: synthetic

<400> SEQUENCE: 12
ugcgcgccug cugccuuccu                                              20

<210> SEQ ID NO 13
<211> LENGTH: 20
<212> TYPE: RNA
<213> ORGANISM: Artificial Sequence
<220> FEATURE:
<223> OTHER INFORMATION: synthetic

<400> SEQUENCE: 13
aacaauacag gacucuuucg                                              20

<210> SEQ ID NO 14
<211> LENGTH: 20
<212> TYPE: RNA
<213> ORGANISM: Artificial Sequence
<220> FEATURE:
<223> OTHER INFORMATION: synthetic

<400> SEQUENCE: 14
ccucguuaaa ggauuuaaag                                              20

<210> SEQ ID NO 15
<211> LENGTH: 20
<212> TYPE: RNA
<213> ORGANISM: Artificial Sequence
<220> FEATURE:
<223> OTHER INFORMATION: synthetic

<400> SEQUENCE: 15
uauuggagcu ggaauuaccg                                              20

<210> SEQ ID NO 16
<211> LENGTH: 20
<212> TYPE: RNA
<213> ORGANISM: Artificial Sequence
```

```
<220> FEATURE:
<223> OTHER INFORMATION: synthetic

<400> SEQUENCE: 16
aaagcucgua guuggaucuu                                                    20

<210> SEQ ID NO 17
<211> LENGTH: 20
<212> TYPE: RNA
<213> ORGANISM: Artificial Sequence
<220> FEATURE:
<223> OTHER INFORMATION: synthetic

<400> SEQUENCE: 17
caaggggcgg ggacgggcgg                                                    20

<210> SEQ ID NO 18
<211> LENGTH: 20
<212> TYPE: RNA
<213> ORGANISM: Artificial Sequence
<220> FEATURE:
<223> OTHER INFORMATION: synthetic

<400> SEQUENCE: 18
ucuuagcuga gugucccgcg                                                    20

<210> SEQ ID NO 19
<211> LENGTH: 20
<212> TYPE: RNA
<213> ORGANISM: Artificial Sequence
<220> FEATURE:
<223> OTHER INFORMATION: synthetic

<400> SEQUENCE: 19
caaagcaggc ccgagccgcc                                                    20

<210> SEQ ID NO 20
<211> LENGTH: 20
<212> TYPE: RNA
<213> ORGANISM: Artificial Sequence
<220> FEATURE:
<223> OTHER INFORMATION: synthetic

<400> SEQUENCE: 20
ggaccgcggu ucuauuuugu                                                    20

<210> SEQ ID NO 21
<211> LENGTH: 20
<212> TYPE: RNA
<213> ORGANISM: Artificial Sequence
<220> FEATURE:
<223> OTHER INFORMATION: synthetic

<400> SEQUENCE: 21
cggcgcaaua cgaaugcccc                                                    20

<210> SEQ ID NO 22
<211> LENGTH: 20
<212> TYPE: RNA
<213> ORGANISM: Artificial Sequence
<220> FEATURE:
<223> OTHER INFORMATION: synthetic

<400> SEQUENCE: 22
cgcucugguc cgucuugcgc                                                    20
```

```
<210> SEQ ID NO 23
<211> LENGTH: 20
<212> TYPE: RNA
<213> ORGANISM: Artificial Sequence
<220> FEATURE:
<223> OTHER INFORMATION: synthetic

<400> SEQUENCE: 23
uaaucaagaa cgaaagucgg                                                    20

<210> SEQ ID NO 24
<211> LENGTH: 20
<212> TYPE: RNA
<213> ORGANISM: Artificial Sequence
<220> FEATURE:
<223> OTHER INFORMATION: synthetic

<400> SEQUENCE: 24
cggucggcau cguuuauggu                                                    20

<210> SEQ ID NO 25
<211> LENGTH: 20
<212> TYPE: RNA
<213> ORGANISM: Artificial Sequence
<220> FEATURE:
<223> OTHER INFORMATION: synthetic

<400> SEQUENCE: 25
guuucccgga agcugcccgg                                                    20

<210> SEQ ID NO 26
<211> LENGTH: 20
<212> TYPE: RNA
<213> ORGANISM: Artificial Sequence
<220> FEATURE:
<223> OTHER INFORMATION: synthetic

<400> SEQUENCE: 26
cugaaacuua aaggaauuga                                                    20

<210> SEQ ID NO 27
<211> LENGTH: 20
<212> TYPE: RNA
<213> ORGANISM: Artificial Sequence
<220> FEATURE:
<223> OTHER INFORMATION: synthetic

<400> SEQUENCE: 27
ggcuuaauuu gacucaacac                                                    20

<210> SEQ ID NO 28
<211> LENGTH: 20
<212> TYPE: RNA
<213> ORGANISM: Artificial Sequence
<220> FEATURE:
<223> OTHER INFORMATION: synthetic

<400> SEQUENCE: 28
cugucaaucc uguccguguc                                                    20

<210> SEQ ID NO 29
<211> LENGTH: 20
<212> TYPE: RNA
<213> ORGANISM: Artificial Sequence
<220> FEATURE:
<223> OTHER INFORMATION: synthetic
```

```
<400> SEQUENCE: 29
gcauggccgu ucuuaguugg                                              20

<210> SEQ ID NO 30
<211> LENGTH: 20
<212> TYPE: RNA
<213> ORGANISM: Artificial Sequence
<220> FEATURE:
<223> OTHER INFORMATION: synthetic

<400> SEQUENCE: 30
gccagagucu cguucguuau                                              20

<210> SEQ ID NO 31
<211> LENGTH: 20
<212> TYPE: RNA
<213> ORGANISM: Artificial Sequence
<220> FEATURE:
<223> OTHER INFORMATION: synthetic

<400> SEQUENCE: 31 gcgucccca acuucuuaga                                               20

<210> SEQ ID NO 32
<211> LENGTH: 20
<212> TYPE: RNA
<213> ORGANISM: Artificial Sequence
<220> FEATURE:
<223> OTHER INFORMATION: synthetic

<400> SEQUENCE: 32
uguuauugcu caaucucggg                                              20

<210> SEQ ID NO 33
<211> LENGTH: 20
<212> TYPE: RNA
<213> ORGANISM: Artificial Sequence
<220> FEATURE:
<223> OTHER INFORMATION: synthetic

<400> SEQUENCE: 33
agcgugugcc uacccuacgc                                              20

<210> SEQ ID NO 34
<211> LENGTH: 20
<212> TYPE: RNA
<213> ORGANISM: Artificial Sequence
<220> FEATURE:
<223> OTHER INFORMATION: synthetic

<400> SEQUENCE: 34
ccguugaacc ccauucguga                                              20

<210> SEQ ID NO 35
<211> LENGTH: 20
<212> TYPE: RNA
<213> ORGANISM: Artificial Sequence
<220> FEATURE:
<223> OTHER INFORMATION: synthetic

<400> SEQUENCE: 35
uacugggaau uccucguuca                                              20

<210> SEQ ID NO 36
```

```
<211> LENGTH: 20
<212> TYPE: RNA
<213> ORGANISM: Artificial Sequence
<220> FEATURE:
<223> OTHER INFORMATION: synthetic

<400> SEQUENCE: 36
ggcggugugu acaaagggca                                                    20

<210> SEQ ID NO 37
<211> LENGTH: 20
<212> TYPE: RNA
<213> ORGANISM: Artificial Sequence
<220> FEATURE:
<223> OTHER INFORMATION: synthetic

<400> SEQUENCE: 37
ggcccucgga ucggccccgc                                                    20

<210> SEQ ID NO 38
<211> LENGTH: 21
<212> TYPE: DNA
<213> ORGANISM: Artificial Sequence
<220> FEATURE:
<223> OTHER INFORMATION: synthetic

<400> SEQUENCE: 38
tgaggtagta ggttgtatag t                                                  21

<210> SEQ ID NO 39
<211> LENGTH: 40
<212> TYPE: DNA
<213> ORGANISM: Artificial Sequence
<220> FEATURE:
<223> OTHER INFORMATION: synthetic

<400> SEQUENCE: 39
aggtgataag actatacaac ctactacctc gaatgtccgt                              40

<210> SEQ ID NO 40
<211> LENGTH: 100
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(20)
<223> OTHER INFORMATION: n is a, c, g, or u

<400> SEQUENCE: 40
gnnnnnnnnn nnnnnnnnnn guuuuagagc uagaaauagc aaguuaaaau aaggcuaguc         60
cguuaucaac uugaaaaagu ggcaccgagu cggugcuuuu                              100

<210> SEQ ID NO 41
<211> LENGTH: 49
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: n is a, c, g, or u
<220> FEATURE:
<221> NAME/KEY: misc_feature
<222> LOCATION: (15)..(34)
<223> OTHER INFORMATION: n is a, c, g, or u
```

```
<220> FEATURE:
<221> NAME/KEY: misc_feature
<222> LOCATION: (37)..(49)
<223> OTHER INFORMATION: n is a, c, g, or u

<400> SEQUENCE: 41
nnnnnnnnnn nnncnnnnnn nnnnnnnnnn nnnnccnnnn nnnnnnnnn         49

<210> SEQ ID NO 42
<211> LENGTH: 49
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(13)
<223> OTHER INFORMATION: n is a, c, g, or u
<220> FEATURE:
<221> NAME/KEY: misc_feature
<222> LOCATION: (15)..(34)
<223> OTHER INFORMATION: n is a, c, g, or u
<220> FEATURE:
<221> NAME/KEY: misc_feature
<222> LOCATION: (37)..(49)
<223> OTHER INFORMATION: n is a, c, g, or u

<400> SEQUENCE: 42
nnnnnnnnnn nnngnnnnnn nnnnnnnnnn nnnnggnnnn nnnnnnnnn         49

<210> SEQ ID NO 43
<211> LENGTH: 71
<212> TYPE: DNA
<213> ORGANISM: Artificial Sequence
<220> FEATURE:
<223> OTHER INFORMATION: synthetic

<400> SEQUENCE: 43
gcggcctcta atacgactca ctatagggt gaatcgcatc gagctgacgt tttagagcta    60
gaaatagcaa g                                                        71

<210> SEQ ID NO 44
<211> LENGTH: 71
<212> TYPE: DNA
<213> ORGANISM: Artificial Sequence
<220> FEATURE:
<223> OTHER INFORMATION: synthetic

<400> SEQUENCE: 44
gcggcctcta atacgactca ctataggggg agcgcaccat cttcttcggt tttagagcta   60
gaaatagcaa g                                                        71

<210> SEQ ID NO 45
<211> LENGTH: 34
<212> TYPE: DNA
<213> ORGANISM: Artificial Sequence
<220> FEATURE:
<223> OTHER INFORMATION: synthetic

<400> SEQUENCE: 45
gtacaagaaa gctgggtcta gaaaaaaagc accg                               34
```

METHODS OF DEPLETING A TARGET MOLECULE FROM AN INITIAL COLLECTION OF NUCLEIC ACIDS, AND COMPOSITIONS AND KITS FOR PRACTICING THE SAME

CROSS REFERENCE TO RELATED APPLICATIONS

This application is a continuation of U.S. application Ser. No. 16/154,414, filed Oct. 8, 2018 and now issued as U.S. Pat. No. 10,988,796; which is a continuation of U.S. application Ser. No. 14/582,081, filed Dec. 23, 2014, now U.S. Pat. No. 10,150,985; which claims priority to U.S. Provisional Patent Application Nos. 61/939,658, filed Feb. 13, 2014, and 62/040,804, filed Aug. 22, 2014; the above applications are herein incorporated by reference.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Oct. 20, 2016, and a size of 9.22 kilobytes. The Sequence Listing filed via EFS-Web is part of the specification and is hereby incorporated in its entirety by reference herein.

INTRODUCTION

Applications in biomedical research often involve the analysis of specific subsets of nucleic acids present in a complex mixture of other sequences—for example, analysis of gene expression by array hybridization, qPCR or massively parallel sequencing. If the sequences of nucleic acids of interest are known, PCR with specific primer sequences can be used to amplify the desired sequences out of the mixture. In some cases, however, it may be desired to analyze multiple different sequences, perhaps where sequence information is not fully known. Messenger RNAs in eukaryotic systems, for example, may be collectively amplified and analyzed using an oligo-dT primer to initiate first strand cDNA synthesis by priming on the poly A tail, thereby reducing or avoiding contamination by unwanted nucleic acids—such as ribosomal RNAs, mitochondrial RNAs and genomic DNA. A requirement for this approach, however, is that the RNA is intact and not degraded, e.g., the poly A tails are not lost or disconnected from the body of the RNA message. Unfortunately, many otherwise useful and interesting biological specimens—such as biopsied material retained as formalin-fixed and paraffin embedded tissue samples (FFPE samples) often suffer from such degradation making oligo-dT priming impractical for such samples. Further, many interesting RNA sequences do not have poly A tails—e.g., non-coding RNAs and non-eukaryotic RNAs. In such cases, random priming can be used to generally amplify all nucleotide species in the sample. However, random priming will also result in the amplification of potentially unwanted sequences—such as genomic DNA or ribosomal RNA.

SUMMARY

Provided are methods of depleting a target nucleic acid from an initial collection of nucleic acids. Aspects of the methods include contacting the initial collection with a nucleic acid guided nuclease specific for the target nucleic acid in a manner sufficient to deplete the target nucleic acid from the initial collection. Depending on a given application, depletion of a target nucleic acid may vary, e.g., where depleting may include cleaving a target nucleic acid in, or selectively separating a target nucleic acid from, the initial collection of nucleic acids. Also provided are compositions and kits for practicing embodiments of the methods.

DETAILED DESCRIPTION

Figure 1:
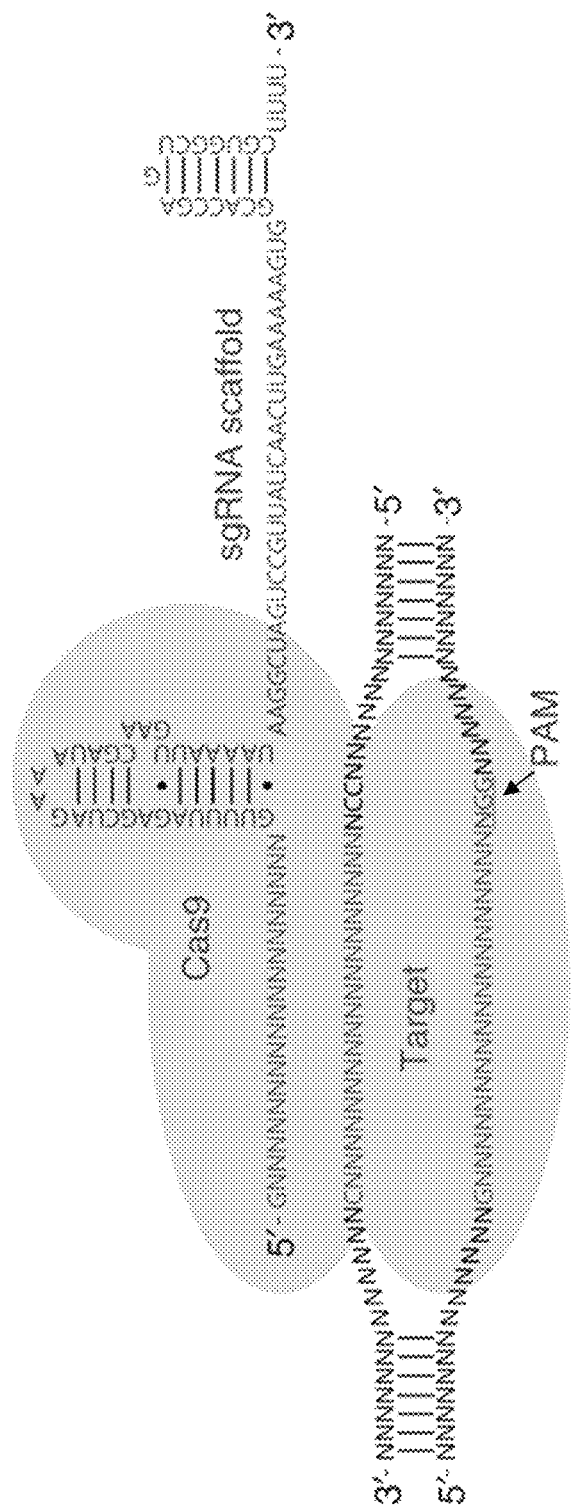
FIG. 1 schematically illustrates a nucleic acid guided nuclease that finds use in certain embodiments of the present disclosure (SEQ ID NOs: 40-42).

Provided are methods of depleting a target nucleic acid from an initial collection of nucleic acids. Aspects of the methods include contacting the initial collection with a nucleic acid guided nuclease specific for the target nucleic acid in a manner sufficient to deplete the target nucleic acid from the initial collection. Depending on a given application, depletion of a target nucleic acid may vary, e.g., where depleting may include cleaving a target nucleic acid in, or selectively separating a target nucleic acid from, the initial collection of nucleic acids. Also provided are compositions and kits for practicing embodiments of the methods.

Before the methods and kits of the present disclosure are described in greater detail, it is to be understood that the methods and kits are not limited to particular embodiments described, as such may, of course, vary. It is also to be understood that the terminology used herein is for the purpose of describing particular embodiments only, and is not intended to be limiting, since the scope of the methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and kits. The upper and lower limits of these smaller ranges may independently be included in the smaller ranges and are also encompassed within the methods and kits, subject to any specifically excluded limit in the stated range. Where the stated range includes one or both of the limits, ranges excluding either or both of those included limits are also included in the methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods and kits similar or equivalent to those described herein can also be used in the practice or testing of the methods and kits, representative illustrative methods and materials are now described.

All publications and patents cited in this specification are herein incorporated by reference as if each individual publication or patent were specifically and individually indicated to be incorporated by reference and are incorporated herein by reference to disclose and describe the methods, kits and/or materials in connection with which the publications are cited. The citation of any publication is for its disclosure prior to the filing date and should not be construed as an admission that the present methods and kits are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and kits, which are, for clarity, described in the context of separate embodiments, may also be provided in combination in a single embodiment. Conversely, various features of the methods and kits, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods and kits. Any recited method can be carried out in the order of events recited or in any other order which is logically possible.

In further describing embodiments of the invention, aspects of embodiments of the subject methods will be described first in greater detail. Thereafter, aspects of embodiments of the kits for practicing the subject methods are described in greater detail.

Methods

Aspects of the invention include methods of selectively depleting a target nucleic acid from an initial collection of nucleic acids. By "depleting" a target nucleic acid is meant reducing the amount of the target nucleic acid in the initial collection of nucleic acids. For example, a target nucleic acid may be depleted by cleavage of the target nucleic acid at one or more locations within the target nucleic acid by one or more nucleic acid guided nuclease(s) in which the nuclease component(s) have nuclease activity. The non-depleted nucleic acids present in the initial collection may then be used in a downstream application of interest, such as nucleic acid amplification, nucleic acid sequencing, gene expression analysis (e.g., by array hybridization, quantitative RT-PCR, massively parallel sequencing, etc.), or any other downstream application of interest.

Alternatively, a target nucleic acid may be depleted by removal (and optionally, recovery) of the target nucleic acid from the initial collection of nucleic acids. As described in more detail below, in certain aspects, removal of a target nucleic acid from the initial collection is effected using a nucleic acid guided nuclease that includes a cleavage-deficient nuclease, which nuclease may include a heterologous component (e.g., a tag) that facilitates removal of the nuclease (and accordingly, the target nucleic acid to which the nuclease is bound) from the initial collection of nucleic acids. By removing/recovering the target nucleic acids from the initial collection, a subsequent collection of nucleic acids enriched for the target sequences may be obtained. This enriched sample (e.g., an exome-enriched sample, a sample enriched for a panel of genes of interest, etc.) may then be used in a downstream application of interest, such as nucleic acid amplification, nucleic acid sequencing, gene expression analysis (e.g., by array hybridization, quantitative RT-PCR, massively parallel sequencing, etc.), or any other downstream application of interest.

According to certain embodiments, depleting target nucleic acids present in the initial collection includes depleting certain species of target nucleic acids by cleavage of such target nucleic acids, and depleting certain other species of target nucleic acids by removal (and optionally, recovery) of such target nucleic acids from the initial collection of nucleic acids.

A target nucleic acid may vary. By "nucleic acid" is meant a polymer of any length, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer, 10,000 bases or longer, 50,000 or more bases composed of nucleotides, e.g., ribonucleotides or deoxyribonucleotides. In some instances, the length of the nucleic acids is 100,000 bases or less, e.g., 75,000 bases or less, including 50,000 bases or less, e.g., 25,000 bases or less, such as 10,000 bases or less, 5,000 bases or less, 2,000 bases or less, 1,000 bases or less, or 500 bases or less.

Depleting a target nucleic acid from the initial collection partially reduces, if not completely eliminates, the presence of the target nucleic acid in the collection. In some instances, the copy number of a given target nucleic acid in the initial collection of nucleic acids is reduced by 5% or more, such as 10% or more, e.g., 25% or more, including 50%, 75%, 90% or more, including embodiments where the presence of the target nucleic acid is completely eliminated. Depleting a target nucleic acid reduces the percentage of the target nucleic acid in a sample with respect to the total nucleic acid in the sample. In certain aspects, after depletion of the target nucleic acid, the percent remaining of the target nucleic acid as compared to the initial amount of target nucleic acid in the sample is 50%, 40%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, or less, including 0.5%, 0.1%, 0.01% or less. By depleting a target nucleic acid in the initial collection, a type of nucleic acid (e.g., a desirable nucleic acid) may be enriched in the collection. According to certain embodiments, in a sample in which a target nucleic acid has been depleted, a type of nucleic acid (e.g., DNA, mRNA, microRNA (miRNA), and/or the like) is enriched in the sample such that the percentage of the type of nucleic acid remaining in the sample relative to the total is 5% or more, such as 10% or more, 25% or more, 30% or more, 40% or more, 50% or more, 60% or more, 70% or more, 75% or more, including 80%, 810%, 82%, 83%, 840%, 85%, 86%, 870%, 880%, 89%, 90%, 91%, 92%, 93%, 94%, 95%, 96%, 97%, 98%, 99%, and 99.5% or more.

The initial collection of nucleic acids is contacted with a nucleic acid guided nuclease. As used herein, a "nucleic acid guided nuclease" is an association (e.g., a complex) that includes a nuclease component and a nucleic acid guide component. The nucleic acid guided nuclease may have nuclease/cleavage activity, e.g., catalyzes the hydrolysis of a target nucleic acid (e.g., a target DNA, a target RNA, etc.) into two or more products thereby depleting the target nucleic acid. Cleavage products may be removed from the sample if desired (e.g., to purify the remaining collection of nucleic acids). In certain embodiments, when it is desirable to deplete certain target nucleic acids by cleavage, the number of distinct nucleic acid guided nucleases used and/or the location(s) of the target nucleic acid cleaved by the nucleic acid guided nuclease(s) may be selected such that all or nearly all of the target nucleic acid fragments are sufficiently small to be removed by nucleic acid purification steps such as ethanol or isopropanol precipitation, spin column purification (e.g., using NucleoSpin® Clean-Up columns by Clontech Laboratories, Inc. (Mountain View, CA)), Solid Phase Reversible Immobilization (SPRI) beads, or the like. When the nuclease component has nuclease activity, the nuclease may generate double-stranded breaks in the target nucleic acid, or the nuclease may be a nuclease that introduces a break in a single strand of a double-stranded target nucleic acid (e.g., the nuclease component may be a nickase).

In certain aspects, the nuclease is a modified nuclease that does not have nuclease activity (e.g., is cleavage deficient) as a result of the modification. Such nucleases may be employed to deplete the target nucleic acid, e.g., upon removal of the target nucleic acid present in a complex formed between the nucleic acid guided nuclease and the target nucleic acid, from the initial collection of nucleic acids, which in certain aspects is facilitated by a tag (e.g., an epitope tag) provided on the nuclease.

Any suitable nuclease component may be employed by a practitioner of the subject methods. The nuclease component may be a wild-type enzyme that exhibits nuclease activity, or a modified variant thereof that retains its nuclease activity. In other aspects, the nuclease component may be a non-nuclease protein operatively linked to a heterologous nuclease (or "cleavage") domain, such that the protein is capable of cleaving the target nucleic acid by virtue of being linked to the nuclease domain. Suitable cleavage domains are known and include, e.g., the DNA cleavage domain of the FokI restriction endonuclease. For example, in certain aspects, the nuclease component of a nucleic acid guided nuclease may be a Cas9 (e.g., a wild-type Cas9 or cleavage deficient Cas9) or other nuclease operably linked to a cleavage domain, such as a FokI cleavage domain. According to certain embodiments, the nuclease is a mutant that is cleavage deficient—e.g., Sp, a Cas9 D10A mutant, a Cas9 H840A mutant, a Cas9 D10A/H840A mutant (see, e.g., Sander & Joung (2014) *Nature Biotechnology* 32:347-355 doi:10.1038/nbt.2842), or any other suitable cleavage deficient mutant. Such a strategy has been successfully employed to confer nuclease activity upon zinc finger and transcription-activator-like effector (TALE) proteins to generate zinc finger nucleases and TALENs, respectively, for genomic engineering purposes (see, e.g., Kim et al. (1996) PNAS 93(3):1156-1160, and US Patent Application Publication Numbers US2003/0232410, US2005/0208489, US2006/0188987, US2006/0063231, and U52011/0301073).

According to certain embodiments, the nuclease domain is derived from an endonuclease. Endonucleases from which a nuclease/cleavage domain can be derived include, but are not limited to: a Cas nuclease (e.g., a Cas9 nuclease), an Argonaute nuclease (e.g., Tth Ago, mammalian Ago2, etc.), S1 Nuclease; mung bean nuclease; pancreatic DNase I; micrococcal nuclease; yeast HO endonuclease; a restriction endonuclease; a homing endonuclease; and the like; see also Mishra (Nucleases: Molecular Biology and Applications (2002) ISBN-10: 0471394610). In certain aspects, the nuclease component of the nucleic acid guided nuclease is a Cas9 nuclease of *Francisella novicida* (or any suitable variant thereof), which uses a scaRNA to target RNA for degradation (see Sampson et al. (2013) Nature 497:254-257).

As described above, according to certain embodiments, the nucleic acid guided nuclease includes a CRISPR-associated (or "Cas") nuclease. The CRISPR/Cas system is an RNA-mediated genome defense pathway in archaea and many bacteria having similarities to the eukaryotic RNA interference (RNAi) pathway. The pathway arises from two evolutionarily (and often physically) linked gene loci: the CRISPR (clustered regularly interspaced short palindromic repeats) locus, which encodes RNA components of the system; and the Cas (CRISPR-associated) locus, which encodes proteins.

There are three types of CRISPR/Cas systems which all incorporate RNAs and Cas proteins. The Type II CRISPR system carries out double-strand breaks in target DNA in four sequential steps. First, two non-coding RNAs (the pre-crRNA array and tracrRNA), are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

CRISPR systems Types I and III both have Cas endonucleases that process the pre-crRNAs, that, when fully processed into crRNAs, assemble a multi-Cas protein complex that is capable of cleaving nucleic acids that are complementary to the crRNA. In type II CRISPR/Cas systems, crRNAs are produced by a mechanism in which a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA in a manner dependent upon base-pairing between the crRNA and the target DNA, and the presence of a short motif in the crRNA referred to as the PAM sequence (protospacer adjacent motif).

The requirement of a crRNA-tracrRNA complex can be avoided by use of an engineered fusion of crRNA and tracrRNA to form a "single-guide RNA" (sgRNA) that comprises the hairpin normally formed by the annealing of the crRNA and the tracrRNA. See, e.g., Jinek et al. (2012) *Science* 337:816-821; *Mali* et al. (2013) *Science* 339:823-826; and Jiang et al. (2013) *Nature Biotechnology* 31:233-239. The sgRNA guides Cas9 to cleave target DNA when a double-stranded RNA:DNA heterodimer forms between the Cas-associated RNAs and the target DNA. This system, including the Cas9 protein and an engineered sgRNA containing a PAM sequence, has been used for RNA guided genome editing with editing efficiencies similar to ZFNs and TALENs. See, e.g., Hwang et al. (2013) *Nature Biotechnology* 31 (3):227.

According to certain embodiments, the nuclease component of the nucleic acid guided nuclease is a CRISPR-associated protein, such as a Cas protein. Non-limiting examples of Cas proteins include Cas1, Cas1 B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain aspects, the nuclease component of the nucleic acid guided nuclease is Cas9.

The Cas9 may be from any organism of interest, including but not limited to, *Streptococcus pyogenes* ("spCas9", Uniprot Q99ZW2) having a PAM sequence of NGG; *Neisseria meningitidis* ("nmCas9", Uniprot C6S593) having a PAM sequence of NNNNGATT; *streptococcus Thermophilus* ("stCas9", Uniprot Q5M542) having a PAM sequence of NNAGAA, and *Treponema denticols* ("tdCas9", Uniprot M2B9U0) having a PAM sequence of NAAAAC. An example nucleic acid guided nuclease that includes a Cas9 nuclease and an sgRNA guide component, in which the sgRNA guide component is aligned with a complementary region of a generalized target nucleic acid, is schematically illustrated in FIG. 1.

In certain aspects, the nuclease component of the nucleic acid guided nuclease is an Argonaute (Ago) nuclease. Ago proteins are a family of evolutionarily conserved proteins central to the RNA interference (RNAi) platform and microRNA (miRNA) function and biogenesis. They are best known as core components of the RNA-induced silencing complex (RISC) required for small RNA-mediated gene regulatory mechanisms. In post-transcriptional gene silencing, Ago guided by a small RNA (e.g., siRNA, miRNA, piRNA, etc.) binds to the complementary transcripts via base-pairing and serve as platforms for recruiting proteins to facilitate gene silencing.

Mammals have eight Argonaute proteins, which are divided into two subfamilies: the Piwi Glade and the Ago Glade. Of the wild-type Ago proteins (Ago1-4, or ElF2C1-4), only Ago2 has endonuclease activity. The crystal structure of full-length human Ago2 (Uniprot Q9UKV8) has been solved. See, e.g., Elkayam et al. (2012) *Cell* 150(1):100-110. Similar to the bacteria counterpart, human Ago2 is a bilobular structure comprising the N-terminal (N), PAZ, MID, and PIWI domains. The PAZ domain anchors the 3'end of the small RNAs and is dispensable for the catalytic activity of Ago2. However, PAZ domain deletion disrupts the ability of the non-catalytic Agos to unwind small RNA duplex and to form functional RISC.

When the nuclease component of the nucleic acid guided nuclease is an Ago nuclease, the nuclease may be an Ago nuclease that cleaves DNA duplexes, RNA duplexes, or DNA-RNA duplexes. The Ago nuclease may be derived from any suitable organism, such as a prokaryotic or eukaryotic organism. In certain aspects, the Ago is a prokaryotic Ago. Prokaryotic Agos of interest include, but are not limited to, *Thermus thermophiles* Ago ("Tth Ago"), such as the Tth Ago nucleases described in Wang et al. (2008) *Nature* 456(7224):921-926; and Wang et al. (2009) *Nature* 461(7265):754-761. DNA-guided DNA interference in vivo using Tth Ago and 5'-phosphorylated DNA guides of from 13-25 nucleotides in length was recently described by Swarts et al. (2014) *Nature* 507:258-261.

The nucleic acid guided nuclease may include a nuclease having nuclease activity (e.g., catalyzes the hydrolysis of a target nucleic acid (e.g., a target DNA, a target RNA, etc.)), or may be a modified nuclease that does not have nuclease activity (e.g., is cleavage deficient) as a result of the modification. In some instances, the nuclease component (e.g., a Cas nuclease component) is a cleavage deficient mutant and the method results in the production of a product composition comprising target nucleic acid/nucleic acid guided nuclease complexes. When part of the resultant complex, the target nucleic acid is no longer free in the collection of nucleic acids, and therefore has been depleted from the initial collection of nucleic acids. In other aspects, the nuclease component of the complex is a cleavage competent nuclease, but the nucleic acid guided nuclease remains bound to a fragment of the target nucleic acid subsequent to cleavage of the target nucleic acid. In some instances, the method further includes separating (e.g., removing) target nucleic acid/nucleic acid guided nuclease complexes (e.g., including a cleavage competent nuclease component and/or a cleavage deficient nuclease component such as a D10A Cas9 mutant, a H840A Cas9 mutant, a D10A/H840A Cas9 mutant, and/or the like) from other constituents of the product composition. Where desired, the nuclease component may include a tag, e.g., an epitope tag, FLAG tag, HA tag, His tag, Myc tag, S-tag, SBP tag, Softag, GST tag, GFP tag, biotin, streptavidin, 6-His tag, etc., e.g., to facilitate separation of the complexes (e.g., by affinity purification) from the other components of the initial collection.

According to certain embodiments, when the method involves the formation of target nucleic acid/nucleic acid guided nuclease complexes, the method further includes recovering the target nucleic acids from the complexes. Any suitable strategy for recovering the target nucleic acids may be employed. Such strategies may include separating the complexes from other constituents of the composition, and then disassociating the target nucleic acids from the nucleic acid guided nucleases. In certain aspects, the nuclease component of the nucleic acid guided nuclease includes a tag (e.g., an epitope tag), and the complexes may be separated from other constituents by affinity purification. For example, the complexes may be immobilized on the surface of a solid phase (e.g., a column, a plate, beads (e.g., agarose or magnetic beads), and/or the like) that includes a binding partner of the tag (e.g., an antibody or other suitable binding partner that binds the tag), and then washed to remove any residual constituents of the composition. The target nucleic acids may then be recovered from the nucleic acid guided nucleases using a suitable elution buffer (e.g., a buffer that includes a protein denaturation agent, such as sodium dodecyl sulfate (SDS)), using a buffer that includes a reagent that digests the nuclease component (e.g., proteinase K), using heat denaturation, and/or the like, to disrupt the interactions between the target nucleic acids and the nucleic acid guided nuclease. Approaches for affinity purification and recovering nucleic acids from protein complexes are described, e.g., in *Methods for Affinity-Based Separations of Enzymes and Proteins* (Munishwar Nath Gupta, ed., Birkhäauser Verlag, Basel-Boston-Berlin, 2002); *Chromatin Immunoprecipitation Assays: Methods and Protocols* (Collas, ed., 2009); and The Protein Protocols Handbook (Walker, ed., 2002). If desired, the separated target nucleic acids may be further purified by alcohol precipitation, column purification, or any other convenient nucleic acid purification strategy.

As summarized above, in certain aspects, the nucleic acid guided nuclease includes a nucleic acid guide component. Any suitable nucleic acid guide component capable of guiding the nuclease component to the target nucleic acid may be employed. The nucleic acid guide component may be single-stranded or double-stranded as appropriate for the particular nuclease component employed.

The nucleic acid guide component may be one or more nucleic acid polymers of any suitable length. In certain aspects, the nucleic acid guide component is a nucleic acid polymer (e.g., a single- or double-stranded RNA or DNA) of from 10 to 200 nucleotides in length, such as from 10 to 150 nucleotides in length, including from 10 to 100, from 10 to 90, from 10 to 80, from 10 to 70, from 10 to 60, from 10 to 50, from 10 to 40, from 10 to 30, from 10 to 25, from 10 to 20, or from 10 to 15 nucleotides in length.

At least a portion of the nucleic acid guide component is complementary (e.g., 100% complementary or less than 100% complementary) to at least a portion of a target nucleic acid of interest. The sequence of all or a portion of the nucleic acid guide component may be selected by a practitioner of the subject methods to be sufficiently complementary to a target nucleic acid of interest to specifically guide the nuclease component to the target nucleic acid. The nucleic acid sequences of target nucleic acids of interest are readily available from resources such as the nucleic acid sequence databases of the National Center for Biotechnology Information (NCBI), the European Molecular Biology Laboratory-European Bioinformatics Institute (EMBL-EBI), and the like. By way of example, when the target nucleic acid(s) of interest is one or both of human 18S rRNA (1.9 kb) and/or human 28S rRNA, the nucleotide sequences of the 18S rRNA are readily available as those of NCBI reference sequences NR_003286.2 and NR_003287.2, respectively.

Once a target nucleic acid is selected, and based on the available sequence information for the target nucleic acid, a nucleic acid guide component may be designed such that all or a portion of the nucleic acid guide component is sufficiently complementary to a target region of the target nucleic acid to specifically guide the nucleic acid guided nuclease under hybridization conditions to the target region of the target nucleic acid, e.g., for cleavage at the target region by the nuclease to deplete the target nucleic acid.

"Hybridization conditions" may include conditions in which the nucleic acid guide component specifically hybridizes to a target region of the target nucleic acid, interactions between the target nucleic acid and nuclease component, or both. Whether a nucleic acid guide component specifically hybridizes to a target nucleic acid is determined by such factors as the degree and length of complementarity between the nucleic acid guide component and the target nucleic acid, and the temperature at which the hybridization/contacting occurs, which may be informed by the melting temperature ($T_M$) of the region of the nucleic acid guide component that is complementary to the target region of the target nucleic acid. The melting temperature refers to the temperature at which half of the nucleic acid guide component-target nucleic acid duplexes remain hybridized and half of the duplexes dissociate into single strands. The $T_m$ of a duplex may be experimentally determined or predicted using the following formula $T_m=81.5+16.6(\log_{10}[\text{Na}^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., Ch. 10). Other more advanced models that depend on various parameters may also be used to predict $T_m$ of nucleic acid guide component-target nucleic acid duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, Part I, chapter 2, "Overview of principles of hybridization and the strategy of nucleic acid probe assays," Elsevier (1993).

According to certain embodiments, the nucleic acid guide component is an RNA guide component (or "guide RNA"). The RNA guide component may include one or more RNA molecules. For example, the RNA guide component may include two separately transcribed RNAs (e.g., a crRNA and a tracrRNA) which form a duplex that guides the nuclease component (e.g., Cas9) to the target nucleic acid. In other aspects, the RNA guide component is a single RNA molecule, which may correspond to a wild-type single guide RNA, or alternatively, may be an engineered single guide RNA. According to certain embodiments, the nucleic acid guide component is an engineered single guide RNA that includes a crRNA portion fused to a tracrRNA portion, which single guide RNA is capable of guiding a nuclease (e.g., Cas9) to the target nucleic acid.

In certain aspects, the nucleic acid guide component is a DNA guide component, e.g., a single-stranded or double-stranded guide DNA. According to certain embodiments, the guide DNA is phosphorylated at one or both ends. For example, the guide DNA may be a 5'-phosphorylated guide DNA oligonucleotide of any suitable length (e.g., any of the lengths set forth above, including for example, from 10 to 30 nucleotides in length). The present inventors have demonstrated that nucleic acid guided nucleases that include such phosphorylated guide DNA oligonucleotides and Tth Ago efficiently deplete a target nucleic acid of interest from an initial collection of nucleic acids based on complementarity between the guide DNA oligonucleotide and the target nucleic acid of interest (see, e.g., the Examples section herein).

As summarized above, the methods of the present disclosure include contacting an initial collection of nucleic acids with a nucleic acid guided nuclease specific for the target nucleic acid of interest in a manner sufficient to deplete the target nucleic acid from the initial collection. In certain aspects, contacting the initial collection of nucleic acids with a nucleic acid guided nuclease includes combining in a reaction mixture the initial collection of nucleic acids, a nucleic acid guide component, and a nuclease component. The nucleic acid guide component and the nuclease component may be stably associated (e.g., as a complex) prior to being added to the reaction mixture, or these components may be added separately for subsequent association with each other and targeting/depletion of the target nucleic acid. In certain aspects, at least a portion of the contacting step occurs under conditions in which the nuclease component is active and able to cleave the target nucleic acid.

The conditions under which the initial collection of nucleic acids is contacted with the nucleic acid guided nuclease may vary. For example, the conditions may include a temperature at which the nucleic acid guide component specifically hybridizes to the target nucleic acid, such as from 0° C. to 10° C. (e.g., 4° C.), from 10° C. to 20° C. (e.g., 16° C.), from 20° C. to 30° C. (e.g., 25° C.), from 30° C. to 40° C. (e.g., 37° C.), from 40° C. to 50° C., from 50° C. to 60° C., from 60° C. to 70° C., or from 70° C. to 80° C. Factors and approaches for achieving specific hybridization between the nucleic acid guide component and the target nucleic acid are described hereinabove. In certain aspects, nucleic acids of the initial collection of nucleic acids are denatured (e.g., heat-denatured) to generate single-stranded nucleic acids prior to the contacting step to facilitate hybridization of the nucleic acid guide component to the target nucleic acid.

According to embodiments in which the nuclease component cleaves the target nucleic acid, the contacting conditions may include a temperature at which the particular nuclease employed is active, e.g., has nuclease activity. Such temperatures may vary, and in certain aspects include temperatures from 0° C. to 10° C. (e.g., 4° C.), from 10° C. to 20° C. (e.g., 16° C.), from 20° C. to 30° C. (e.g., 25° C.), from 30° C. to 40° C. (e.g., 37° C.), from 40° C. to 50° C., from 50° C. to 60° C., from 60° C. to 70° C., or from 70° C. to 80° C.

The nuclease activity of certain nucleases depends on the presence of one or more cofactors. When such a nuclease component is employed to practice the subject methods, the contacting conditions may include providing any necessary cofactors to the reaction mixture. In certain aspects, the cofactor(s) is one or more divalent cations, such as $Mg^{2+}$, $Mn^{2+}$, $Ca^{2+}$, and/or the like.

The reaction mixture may include one or more buffers (e.g., a Tris buffer, a PBS buffer, or the like) to ensure that the contacting occurs a suitable pH, e.g., at which the nuclease exhibits nuclease activity. For example, the contacting conditions may include the pH of the reaction mixture being from pH 4.5 to 8.5, such as from 4.5 to 5.5, from 5.5 to 6.5, from 6.5 to 7.5, or from 7.5 to 8.5.

The contacting step may be performed such that the final concentrations of the initial collection of nucleic acids, the nucleic acid guide component, and the nuclease component are suitable to deplete the target nucleic acid. For example, the final concentration of the initial collection of nucleic acids may be from 0.1 μg/μl to 10 μg/μl, the final concentration of the nucleic acid guide component may be from 25 pM to 50 μM, and the final concentration of the nuclease component may be from 25 pM to 50 μm.

Aspects of the invention include methods of making a nucleic acid guided nuclease, e.g., any of the nucleic acid guided nucleases described elsewhere herein. Approaches for making the nucleic acid guided nuclease may vary. In certain aspects, the methods include expressing a nucleic acid guide component and a nuclease component from the same or different expression plasmids. Plasmids and associated protocols for expressing a nucleic acid guide component and/or a nuclease component are commercially available and include, e.g., the GeneArt® CRISPR nuclease vectors (Life Technologies, Carlsbad, CA).

Figure 2:
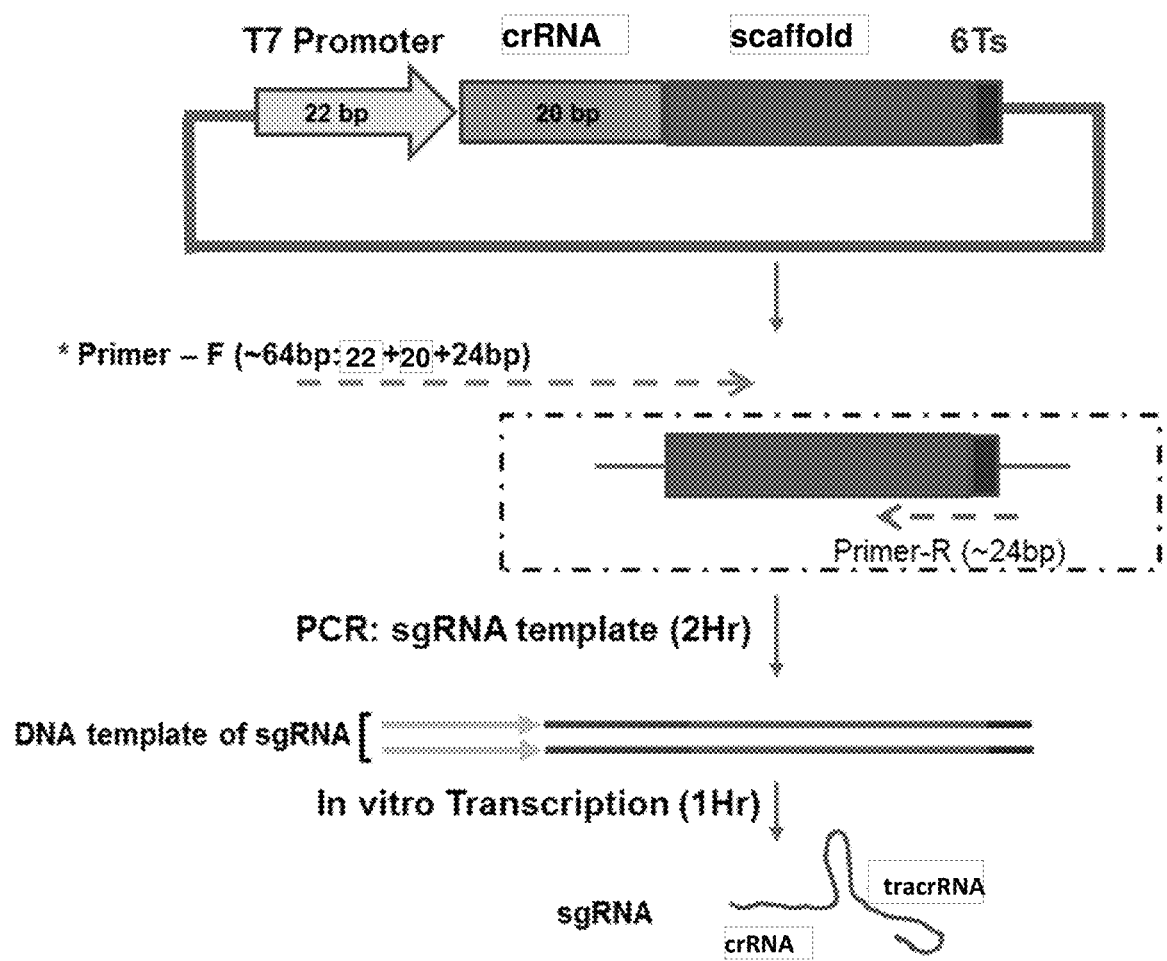
FIG. 2 schematically illustrates a method for producing a nucleic acid guide component according to one embodiment of the present disclosure.
Figures 3, 4:
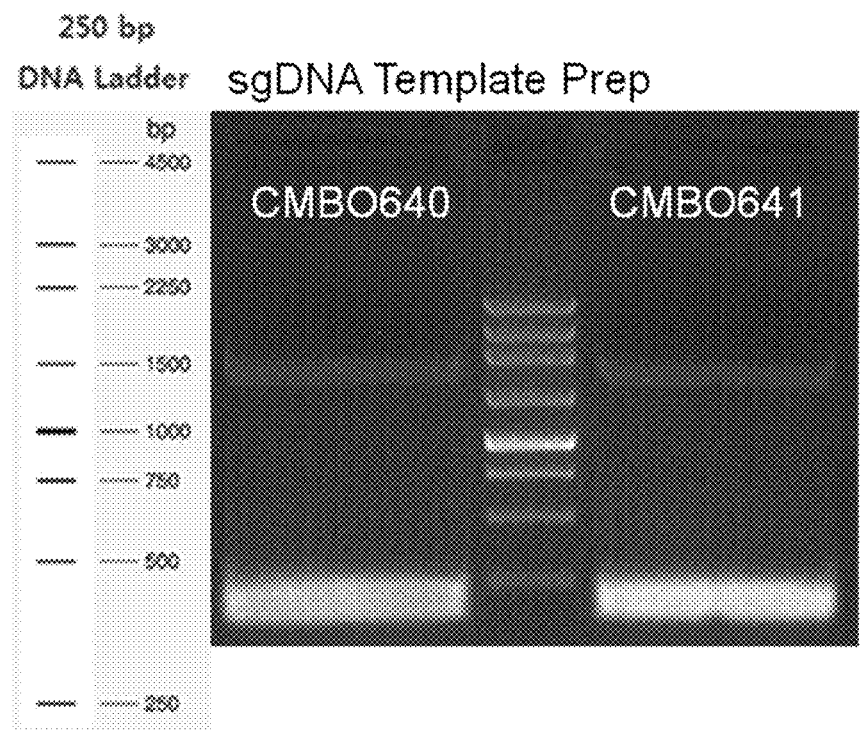
FIG. 3 shows three examples of oligonucleotides (T7-T1-AcGFP-SEQ ID NO: 43; T7-T2-AcGFP-SEQ ID NO: 44; T7-Rev-SEQ ID NO: 45) that find use in the method schematically illustrated in FIG. 2.
FIG. 4 shows an image of template nucleic acids visualized by gel electrophoresis. The template nucleic acids find use in producing nucleic acid guide components by in vitro transcription according to one embodiment of the present disclosure.

According to certain embodiments, the present disclosure provides PCR-based methods of producing a nucleic acid guide component specific for a target nucleic acid of interest. One embodiment of such methods is schematically illustrated in FIG. 2. As shown, a user may design an oligonucleotide primer (shown here as the forward "F" primer) that includes: a sequence complementary to a promoter sequence of interest (e.g., a T7, U6, T3 or other promoter); a sequence complementary to an sgRNA guide sequence specific for a target nucleic acid of interest (e.g., specific for a target cDNA transcribed from an rRNA); and a sequence complementary to at least a portion of an sgRNA scaffold sequence. This forward primer may be used in conjunction with an oligonucleotide primer (shown here as the reverse "R" primer) having a sequence complementary to at least a portion of the sgRNA scaffold sequence and any other useful sequences (e.g., a poly dT tract) for producing an sgRNA. PCR amplification using these primers and a template that includes the scaffold and any other desirable elements produces a template (designated in FIG. 2 as the "DNA template of sgRNA") from which a particular sgRNA may be transcribed by in vitro transcription and employed in conjunction with a nuclease for, e.g., selective depletion of a target nucleic acid according to the methods of the present disclosure. Shown in FIG. 3 are example forward (T7-T1-AcGFP, SEQ ID NO: 41; and T7-T2-AcGFP, SEQ ID NO: 42) and reverse (T7-Rev, SEQ ID NO: 43) oligonucleotides for producing templates from which sgRNAs may be produced by in vitro transcription, e.g., according to the embodiment shown in FIG. 2. The sequence outlined with dashed rectangles is the T7 promoter sequence. Underlined sequences are 20 bp crRNA sequences. A polyA sequence is outlined with a solid rectangle.

The initial collection of nucleic acids may vary. Examples of initial collection of nucleic acids of interest include collections of double-stranded nucleic acids (e.g., double-stranded DNA), collections of single stranded nucleic acids (e.g., single-stranded RNA or DNA), mixed collections of double and single stranded nucleic acids, etc. The complexity of the initial collection may also vary, where in some instances the collection includes 5 or more, 10 or more, 25 or more, 50 or more, 100 or more, 250 or more, 500 or more, 1000 or more, 5,000 or more, including 10,000, 100,000 or more, 500,000 or more, 1 million or more, 100 million or more, or 1 billion or more distinct nucleic acids of differing sequence. The initial collection of nucleic acids may include deoxyribonucleic acids, ribonucleic acids, or mixtures thereof.

In certain aspects, the initial collection of nucleic acids of interest is a collection of nucleic acids (e.g., undesired and desired nucleic acids) isolated from a nucleic acid source of interest, including but not limited to, a nucleic acid sample isolated from a single cell, a plurality of cells (e.g., cultured cells), a tissue, an organ, or an organism, e.g., bacteria, yeast, or a collection of organisms (such as a metagenomic sample, e.g., sea water containing multiple organisms, a fecal sample containing many distinct bacterial species, a buccal swab, etc.), or the like. The term "sample", as used herein, relates to a material or mixture of materials, typically, although not necessarily, in liquid form, containing nucleic acids and/or proteins which one desires to deplete from an initial collection (e.g., by cleavage or removal as described elsewhere herein). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source. According to certain embodiments, the initial collection of nucleic acids of interest is not genomic DNA.

Any convenient protocol for isolating nucleic acids from such sources, as well as reagents and kits designed for isolating nucleic acids from such sources, may be employed. For example, kits for isolating nucleic acids from a source of interest—such as the NucleoSpin®, NucleoMag® and NucleoBond® genomic DNA or RNA isolation kits by Clontech Laboratories, Inc. (Mountain View, CA)— are commercially available. In certain aspects, the nucleic acid is isolated from a fixed biological sample, e.g., formalin-fixed, paraffin-embedded (FFPE) tissue. Nucleic acids from FFPE tissue may be isolated using commercially available kits—such as the NucleoSpin® FFPE DNA or RNA isolation kits by Clontech Laboratories, Inc. (Mountain View, CA).

According to certain embodiments, the initial collection of nucleic acids of interest is produced from a precursor collection of nucleic acids of interest. For example, the initial collection of nucleic acids of interest may be a collection of DNAs (e.g., cDNAs) transcribed from a precursor collection of nucleic acids of interest (e.g., RNAs). In certain aspects, the initial collection of nucleic acids of interest is a collection of cDNAs transcribed from a precursor collection of RNAs of interest, where the precursor collection of RNAs of interest include mRNAs, miRNAs, rRNAs, and/or the like, and the target nucleic acid to be depleted is cDNA transcribed from rRNAs present in the precursor collection of nucleic acids.

Generating a collection of cDNAs of interest from a precursor collection of RNAs of interest may include carrying out a reverse transcription reaction by combining the precursor collection of RNAs of interest with a suitable polymerase, dNTPs, buffer components that establish an appropriate pH, one or more salts (e.g., KCl), one or more metal cofactors (e.g., $Mg^{2+}$ or $Mn^{2+}$), and the like, under conditions suitable for a polymerase-mediated extension reaction to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, CA)), betaine, single-stranded binding proteins (e.g., T4 Gene 32, cold shock protein A (CspA), and/or the like), DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions.

Polymerases that find use in generating a collection of cDNAs of interest from a precursor collection of RNAs of interest include, but are not limited to, reverse transcriptases, such as a retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof. For example, the reverse transcriptase may be a Moloney Murine Leukemia Virus reverse transcriptase (MMLV RT) or a *Bombyx mori* reverse transcriptase (e.g., *Bombyx mori* R2 non-LTR element reverse transcriptase). In certain aspect, the polymerase is capable of template switching. Template switching polymerases are commercially available and include SMARTScribe™ reverse transcriptase and PrimeScript™ reverse transcriptase available from Clontech Laboratories, Inc. (Mountain View, CA). In certain aspects, a mix of two or more different polymerases is added to the reaction mixture, e.g., for improved processivity, proof-reading, and/or the like. In certain aspects, the polymerase (e.g., a reverse transcriptase such as an MMLV RT or a *Bombyx mori* RT) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

In certain aspects, the initial collection of nucleic acids of interest is produced from a precursor collection of nucleic acids of interest by shearing/fragmenting the precursor collection of nucleic acids of interest, e.g., when it is desirable to control the size of the nucleic acids in the initial collection of nucleic acids of interest. Shearing/fragmentation strategies include, but are not limited to, passing a precursor collection of nucleic acids of interest one or more times through a micropipette tip or fine-gauge needle, nebulizing the sample, sonicating the sample (e.g., using a focused-ultrasonicator by Covaris, Inc. (Woburn, MA)), bead-mediated shearing, enzymatic shearing (e.g., using one or more DNA- or RNA-shearing enzymes), chemical based fragmentation, e.g., using divalent cations (e.g., $Mg^{2+}$, $Mn^{2+}$, and/or $Zn^{2+}$), fragmentation buffer (e.g., a high pH buffer), and/or heat, or any other suitable approach for shearing/fragmenting a precursor collection of nucleic acids of interest to generate a shorter initial collection of nucleic acids of interest. In certain aspects, the initial collection of nucleic acids of interest generated by shearing/fragmentation has a length of from 50 to 10,000 nucleotides, from 100 to 5000 nucleotides, from 150 to 2500 nucleotides, from 200 to 1000 nucleotides, e.g., from 250 to 500 nucleotides in length, for example.

According to certain embodiments, the initial collection of nucleic acids of interest includes nucleic acids (e.g., double-stranded DNA, such as double-stranded cDNA) having one or more sequencing adapter constructs at one or both ends of the nucleic acids. By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™ MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Such an initial collection of nucleic acids finds use, e.g., when it is desirable to determine the sequence(s) of nucleic acids present in the initial collection of nucleic acids using a sequencing platform.

When the initial collection of nucleic acids (e.g., cDNAs) includes sequencing platform adapter constructs, the methods of the present disclosure find use in depleting one or more subpopulations of target nucleic acids in the initial collection (e.g., undesirable sequences such as cDNAs transcribed from rRNAs or particular subtypes thereof; or desirable sequences which are depleted by removal from the initial collection, recovered to produce a sample enriched for the desirable nucleic acids), followed by sequencing the desirable nucleic acids. On sequencing platforms that utilize adapter sequences at both ends of a nucleic acid to be sequenced (e.g., an Illumina®—Ion Torrent™-based platform), a single cleavage event by a nucleic acid guided nuclease in a target nucleic acid (e.g., a cDNA transcribed from an rRNA) renders the fragmented target nucleic acid invisible to the sequencer.

According to certain embodiments, the sequencing platform adapter construct includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

In some instances, the subject methods include contacting the initial collection of nucleic acids with a plurality (e.g., a "pool" or "library") of two or more distinct nucleic acid guided nucleases. The nucleic acid guided nucleases may be distinct in any desired respects. For example, the methods may employ a pool of nucleic acid guided nucleases in which the pool includes a single type of nuclease component (e.g., a nuclease which may have nuclease activity or, alternatively, be cleavage deficient) and two or more species of nucleic acid guide components having different nucleotide sequences. The two or more species of nucleic acid guide components may be designed such that the resulting different nucleic acid guided nucleases target multiple regions of a single target nucleic acid, target multiple different target nucleic acids, target multiple regions of multiple different target nucleic acids, etc.

Alternatively, or additionally, the plurality of two or more distinct nucleic acid guided nucleases may include two or more types of nuclease components. For example, the methods may employ a pool/library of any desired combination of nucleases that differ from one another with respect to the origin of the nuclease (e.g., nucleases from different prokaryotic and/or eukaryotic species), nucleases that differ from one another with respect to nuclease activity (e.g., the pool/library may include one or more nucleases that have nuclease activity, one or more nucleases that are cleavage deficient, one or more nickases, or any combination thereof), PAM sequence (e.g., the pool/library may include nucleases that utilize guide nucleic acids having different PAM sequences), and any other combination of nuclease components suitable for depleting one or more target nucleic acids from the initial collection. As set forth above, a pool of different nuclease components may be used in conjunction with a pool of different nucleic acid guide components to achieve a desired level of depletion of a desired number of target nucleic acids. The depletion may include cleaving target nucleic acids present in the initial collection (e.g., one or more ribosomal and/or mitochondrial RNAs), removing target nucleic acids from the initial collection (e.g., to produce a nucleic acid sample enriched for the target nucleic acids removed from the initial collection), or both.

As such, aspects of the present disclosure include methods of selectively depleting a subpopulation of nucleic acids (e.g., rRNA- and/or mtRNA-derived nucleic acids) from an initial collection of nucleic acids. In such embodiments, the methods may include contacting the initial collection of nucleic acids with a library of nucleic acid guided nucleases in a manner sufficient to deplete the subpopulation from the initial collection, where the library includes two or more distinct nucleic acid guided nucleases specific for two or more members and/or multiple regions of a single member of the subpopulation of nucleic acids. In these embodiments, the size of the library may vary. For example, the library may include 2 or more, 3 or more, 4 or more, 5 or more, 10 or more, 25 or more, 100 or more, 500 or more, 1000 or more, 10000 or more, 50000 or more, 100000 or more, 500000 or more, or 1 million or more distinct nucleic acid guided nucleases, etc. In certain aspects, the library includes two or more, but 1 million or less, 500000 or less, 100000 or less, 50000 or less, 10000 or less, 1000 or less, 500 or less, 100 or less, 25 or less, 10 or less, 5, 4, or 3 distinct nucleic acid guided nucleases. Aspects of the present disclosure further include methods of making a library of nucleic acid guided nucleases. Such methods may include producing a plurality of distinct nucleic acid guide components using the PCR-based approach shown in FIG. 2 and described above. In certain embodiments, the methods include combining a plurality of distinct guide nucleic acids with a one or more distinct nucleases in a manner sufficient to produce the library of nucleic acid guided nucleases. The nuclease may vary, and in some instances is a Cas nuclease (e.g., Cas9) or Ago nuclease, which independently may or may not have cleavage activity. The size of the produced library may vary, and in some instances includes 2 or more, 3 or more, 4 or more, 5 or more, 10 or more, 25 or more, 100 or more, 500 or more, 1000 or more, 10,000 or more, 50,000 or more, 100,000 or more, 500,000 or more, or 1 million or more distinct nucleic acid guided nucleases. In certain aspects, the produced library includes two or more, but 1 million or less, 500,000 or less, 100,000 or less, 50,000 or less, 10,000 or less, 1000 or less, 500 or less, 100 or less, 25 or less, 10 or less, 5, 4, or 3 distinct nucleic acid guided nucleases. In some instances, the nucleic acid guides include separate crRNA and tracrRNA, or a component that includes functional elements thereof, e.g., an sgRNA. In some instances, the methods include producing the nucleic acid guides, e.g., by expressing the nucleic acid guides from plasmids encoding the nucleic acid guides, or by PCR and in vitro transcription, such as described in greater detail above and shown in FIG. 2. According to certain embodiments, the nucleic acid guides are produced by solid phase synthesis (e.g., as in standard oligonucleotide synthesis).

In some instances, the nucleic acid guided nucleases of the produced library each include a nucleic acid guide component (e.g., a RNA or DNA guide component) and a nuclease component, e.g., a Cas nuclease component (such as Cas9), an Argonaute nuclease component (e.g., Tth Ago, Ago2, or the like). The nuclease component may exhibit cleavage activity or be a cleavage deficient mutant. Where desired, the nuclease component may further include a tag, such as described above.

Also provided by the present disclosure are compositions. In certain aspects, the compositions include a plurality of distinct nucleic acid guided nucleases. The plurality of distinct nucleic acid guided nucleases may include 2 or more, 3 or more, 4 or more, 5 or more, 10 or more, 25 or more, 100 or more, 500 or more, 1000 or more, 10,000 or more, 50,000 or more, 100,000 or more, 500,000 or more, or 1 million or more distinct nucleic acid guided nucleases, etc. In certain aspects, the plurality of distinct nucleic acid guided nucleases includes two or more, but 1 million or less, 500,000 or less, 100,000 or less, 50,000 or less, 10,000 or less, 1000 or less, 500 or less, 100 or less, 25 or less, 10 or less, 5, 4, or 3 distinct nucleic acid guided nucleases.

According to certain embodiments, the distinct nucleic acid guided nucleases are distinct based on: the nucleic acid guided nucleases having differing nuclease components; and/or the nucleic acid guided nucleases having nucleic acid guide components of differing nucleotide sequence. For example, the distinct nucleic acid guided nucleases may target different regions of the same target nucleic acid based on the guide components having differing sequences complementary to different regions of the same target nucleic acid, and/or the distinct nucleic acid guided nucleases may target different target nucleic acids based on the guide components having differing sequences complementary to the different target nucleic acids and/or different species of nucleases (e.g., different Cas9 species) with different PAM sequence requirements so as to broaden the array of target sequences.

The subject compositions may be present in any suitable environment. According to one embodiment, the composition is present in a reaction tube (e.g., a 0.2 mL tube, a 0.6 mL tube, a 1.5 mL tube, or the like) or a well. In certain aspects, the composition is present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells. In certain embodiments it may be convenient for the reaction to take place on a solid surface or a bead, in such case, the initial collection of nucleic acids or the nucleic acid guided nuclease(s) may be attached to the solid support or bead by methods known in the art—such as biotin linkage or by covalent linkage) and reaction allowed to proceed on the support.

Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

The nucleic acid targeted for depletion can be any target nucleic acid selected by a practitioner of the subject methods. According to one embodiment, the target nucleic acid is an initial RNA (e.g., an rRNA or mtRNA, and not a reverse transcription product of an RNA). In certain aspects, the target nucleic acid is a reverse (DNA) transcription product of an initial RNA (e.g., an rRNA or mtRNA). The RNA (e.g., the initial transcribed RNA) may be any type of RNA (or sub-type thereof) including, but not limited to, a ribosomal RNA (rRNA), a mitochondrial RNA (mtRNA), a microRNA (miRNA), a messenger RNA (mRNA), transfer RNA (tRNA), a small nucleolar RNA (snoRNA), a small nuclear RNA (snRNA), a long non-coding RNA (lncRNA), a non-coding RNA (ncRNA), a small interfering RNA (siRNA), a transacting small interfering RNA (ta-siRNA), a natural small interfering RNA (nat-siRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, and any combination of RNA types thereof or subtypes thereof. When the target nucleic acid is a transcription product of an initial RNA, the methods may include depleting all types of such transcription products in the sample (e.g., ribosomal RNA, transfer RNA, microRNA, and the like), or one or more particular types of such transcription products. In certain aspects, the target nucleic acid is a transcription product of a ribosomal RNA (rRNA) template. The rRNA template in such instances may be a eukaryotic 28S, 26S, 25S, 18S, 5.8S, 5S rRNA, or any combination thereof. In other aspects, the rRNA template may be a prokaryotic 23S, 16S, 5S rRNA, or any combination thereof. The subject methods find use in depleting RNA transcription products other than those produced from ribosomal RNAs. For example, the target nucleic acid may be a transcription product of a messenger RNA (mRNA), e.g., a highly expressed but clinically irrelevant mRNA from a pool of total RNA or mRNA (e.g., a globulin mRNA in a sample of total or polyA±blood RNA). Other types of RNA transcription products may be targeted for depletion, including a mitochondrial RNA (mtRNA), a precursor messenger RNA (pre-mRNA), a micro RNA (miRNA), a transfer RNA (tRNA), and any combination thereof. The target transcription product may be a product of RNA from a particular organism, such as bacterial RNA or yeast RNA. According to certain embodiments, the target nucleic acid is not genomic DNA.

In certain aspects, the target molecule is a target nucleic acid, and the target nucleic acid is a deoxyribonucleic acid (DNA), e.g., intronic or inter-geneic DNA when it is desired to enrich a sample for exonic DNA (e.g., to enrich a sample for nucleic acids corresponding to the exome of a species of interest) by cleaving intronic or inter-geneic DNA present in the initial collection, or by capturing the exonic sequences directly. In certain aspects, DNA-based plasmids/vectors such as those used for in vitro transcription may be targeted for depletion by cleavage, e.g., after completion of an in vitro transcription reaction to enrich a nucleic acid sample for newly transcribed RNA.

When practicing the methods of the present disclosure, the nucleic acid guided nuclease(s) may be designed such that the frequency of cleavage and resulting fragment sizes of a particular target nucleic acid is selected by a practitioner of the subject methods. For example, as described above, two or more nucleic acid guided nucleases that target different sequences within a target nucleic acid may be used in a multiplex fashion when it is desirable to cleave the target nucleic acid into 3 or more fragments. The targeted sequences of the target nucleic acid may be chosen to produce fragments of a desired size, e.g., fragments which are small enough to be removed from the sample using a spin column, alcohol precipitation, and/or the like.

Utility

The subject methods find use in a variety of different applications, e.g., where it is desirable to deplete irrelevant and/or undesired molecules from a sample of interest; where it is desirable to deplete nucleic acids of interest by removing the nucleic acids of interest from the sample for subsequent recovery (thereby producing a sample enriched for the nucleic acids of interest; and/or the like. By depleting the irrelevant and/or undesired molecules, or removing desirable molecules to produce an enriched sample, the complexity of the sample is reduced and the sample is enriched for molecules of interest. When the molecules of interest are nucleic acids, reduced complexity and enrichment of nucleic acids of interest may facilitate and/or improve the results of downstream applications such as nucleic acid amplification, nucleic acid sequencing, gene expression analysis (e.g., by array hybridization, quantitative RT-PCR, massively parallel sequencing, etc.), the preparation of pharmaceutical compositions in which a therapeutic nucleic acid of interest is to be included, and any other applications in which reduced sample complexity and enrichment of nucleic acids of interest is beneficial.

By way of example, certain embodiments of the subject methods include depleting nucleic acids from a sequencing library. For example, the initial collection may be a collection of nucleic acids to be sequenced on a sequencing platform of interest (e.g., a high-throughput or "next generation" sequencing platform such as an Illumin®—or Ion Torrent®-based sequencing platform), but the collection includes irrelevant/undesirable nucleic acids which may complicate or interfere with obtaining the sequences of nucleic acids of interest (e.g., research or clinical interest) in the collection. The irrelevant/undesirable nucleic acids may be reduced or eliminated using the methods of the present disclosure, e.g., by nucleic acid guided nuclease-mediated cleavage, or by producing a sequencing sample that is enriched for sequences of interest by removal of such sequences from the initial collection using the methods of the present disclosure.

In certain aspects, depletion of a target nucleic acid (e.g., an irrelevant/undesirable nucleic acid, such as a nucleic acid derived from an rRNA, an mtRNA, or the like) renders the target nucleic acid invisible to the sequencing platform. That is, the depleted (e.g., cleaved) target nucleic acid is no longer suitable for sequencing on the sequencing platform of interest. For example, Illumina®- and Ion Torrent®-based sequencing platforms require nucleic acids having adapters at each end of the nucleic acids. According to certain embodiments, the nucleic acids of the initial collection of nucleic acids include sequencing adapters at each end, where selective depletion of the target nucleic acid (e.g., cDNAs transcribed from rRNA) includes cleaving the target nucleic acid into at least two fragments, none of which will include sequencing adapters at each end as required for sequencing on an Illumina®—or Ion Torrent®-based sequencing platform. As such, the target nucleic acid is rendered invisible to the sequencing platform, thereby reducing the "load" on the sequencing platform and the complexity of the sequencing results.

In certain aspects, when the sequencing platform of interest only requires the nucleic acid to include an adapter at a single end of a nucleic acid, the target nucleic acid can be rendered unsuitable for sequencing on the platform by, e.g., cleaving the target nucleic acid such that the length of most or all of the resulting fragments are too short to be sequenced on the sequencing platform. This may be accomplished by cleaving the target nucleic acid at a single location, or at two or more locations within the target nucleic acid, to generate fragments of insufficient length to be sequenced on the sequencing platform, e.g., because the platform requires nucleic acids of greater length, or the fragments are lost during a purification procedure (e.g., bead purification, such as SPRI bead-based purification) prior to sequencing. The location(s) to be cleaved and the distance(s) between cleavage sites may be selected by a practitioner of the subject methods to generate cleavage fragments of the desired length, e.g., using available nucleic acid sequence information for a target nucleic acid of interest and designing nucleic acid guide component(s) with sequence complementarity to the selected cleavage site(s). In this way, the target nucleic acid is rendered invisible to the sequencing platform and the load on the sequencing platform and complexity of the sequencing results is reduced.

As described above, the methods of the present disclosure also find use in selectively recovering one or more types of nucleic acids of interest from an initial collection of nucleic acids. For example, in certain aspects, depleting one or more types of target nucleic acids from the initial collection of nucleic acids includes capturing the target nucleic acid via formation of target nucleic acid/nucleic acid guided nuclease complexes, and then recovering the target nucleic acids from the complexes, e.g., for downstream analysis (e.g., quantitative analysis, sequence analysis, and/or the like).

Approaches for target nucleic acid capture and recovery include, e.g., affinity-based approaches (which in certain aspects is facilitated by the nuclease component including an epitope/affinity tag), as described hereinabove. Accordingly, the subject methods find use in selectively obtaining one or more target nucleic acids of interest from collections of nucleic acids, which in certain aspects are complex collections of nucleic acids (e.g., a collection of cDNAs produced by reverse transcription of a total RNA sample, exons from a genomic library, or any other complex nucleic acid collections of interest).

Kits

Also provided by the present disclosure are kits useful for practicing the subject methods. The kits may include one or more of any of the components described above in relation to the subject methods and compositions. For example, the kits may include a primer and a template for generating PCR amplification products from which a nucleic acid guide component may be produced by in vitro transcription. Such reagents may include any reagents useful in practicing the method for producing a nucleic acid guide component (e.g., an sgRNA) shown in FIG. 2 and described hereinabove. According to certain aspects, the kit includes a reverse primer for use in conjunction with a forward primer provided by a user of the kit, where at least a portion of the forward primer includes a nucleic acid sequence complementary to a target nucleic acid selected for depletion by the user.

In some instances, the kits include: a vector that includes a sgRNA scaffold template domain; a reverse primer configured for use with the vector in a PCR reaction;

and an RNA polymerase. In some instances, the reverse primer comprises a polyA domain and an sgRNA scaffold domain. While the RNA polymerase may vary, in some embodiments the RNA polymerase is a T7 polymerase. Where desired, the kit further includes one or more of a DNA polymerase; a PCR buffer; a nuclease (e.g., a Cas, Ago, or other nuclease) which may or may not have cleavage activity; a control nucleic acid; etc.

Components of the subject kits may be present in separate containers, or multiple components may be present in a single container. For example, when the kit includes a primer for generating a template DNA from which an RNA guide component is produced by in vitro transcription, the primer may be provided in a separate container, or in a container that includes a second component of the kit (e.g., a buffer or the like).

In addition to the above-mentioned components, the subject kit may further include instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXAMPLES

Example 1: Depletion of a Target PCR Fragment

In this example, a nucleic acid guided nuclease was produced and, as proof of concept, used to deplete a PCR product having a target sequence corresponding to an rRNA sequence. Using the method outlined in FIG. 2 and described above, two distinct sgDNA templates (CMB0640 and CMBO641) were generated by PCR using the Advantage® HD polymerase (Clontech Laboratories, Mountain View, CA). The PCR products are seen as the main (lower) bands in the gel image shown in FIG. 4. Between 100-120 ng of the templates were used in an in vitro transcription reaction in accordance with the Takara T7 RNA polymerase manual to produce the corresponding sgRNAs.

Figure 5:
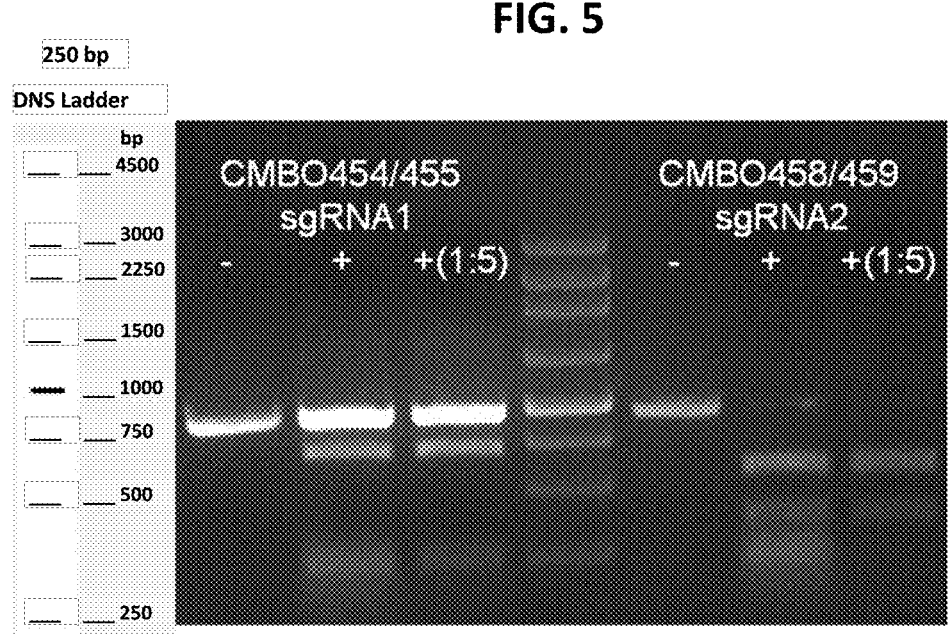
FIG. 5 shows an image of nucleic acids visualized by gel electrophoresis. The image demonstrates the cleavage of a target nucleic acid using a nucleic acid guided nuclease according to one embodiment of the present disclosure.

The in vitro transcribed CMB0640 (72 ng/µl) and CMBO641 (90 ng/µl) sgRNAs were then tested for their ability, when combined with Cas9 (500 ng), to cleave a PCR product (260 ng) having a sequence corresponding to an rRNA sequence. The results are provided in FIG. 5. As shown, combining Cas9, the COMBO640 and/or COMBO641 sgRNAs, and the PCR product results in cleavage of the PCR product.

Example 2: Multiplex Depletion of DNAs Corresponding to Full-Length 18S rRNA

Figure 6:
FIG. 6 shows an image of nucleic acids visualized by gel electrophoresis. The image demonstrates the simultaneous cleavage of two different target nucleic acids using nucleic acid guided nucleases according to one embodiment of the present disclosure.

In this example, it is shown that two different sgRNAs having different target sequence specificities can be used in conjunction (i.e., in a multiplex fashion) to deplete a target DNA having a sequence corresponding to full-length 18S rRNA. As shown in the gel image provided in FIG. 6, a nucleic acid guided nuclease that includes Cas9 and a first sgRNA ("sgRNA1", fourth lane from the left) and a nucleic acid guided nuclease that includes Cas9 and a second sgRNA ("sgRNA2", fifth lane from the left) are separately able to cleave at different locations a target DNA having a sequence corresponding to full-length 18S rRNA. When the two nucleic acid guided nucleases are both combined with the target DNA (sixth lane from the left), the target DNA is cleaved at both of the respective cleavage sites, indicating that multiplexed target depletion occurred.

Example 3: Depletion of Undesirable Sequences from Next Generation Sequencing Libraries In this example, the ability of nucleic acid guided nucleases to deplete unwanted sequences from next generation sequencing libraries was tested. A next generation sequencing library of cDNAs transcribed from human brain total RNA was treated with a sgRNA/Cas9 nucleic acid guided nuclease to deplete cDNAs corresponding to 18S rRNA by cleaving at position 1022-1041 of the cDNAs corresponding to 18S rRNA prior to sequencing the library. The resulting sequences were mapped to the rRNA and the number of reads overlapping 1022-1041 was divided by the total number of reads mapping to rRNA. The ratio was plotted and normalized to control.

Figure 7:
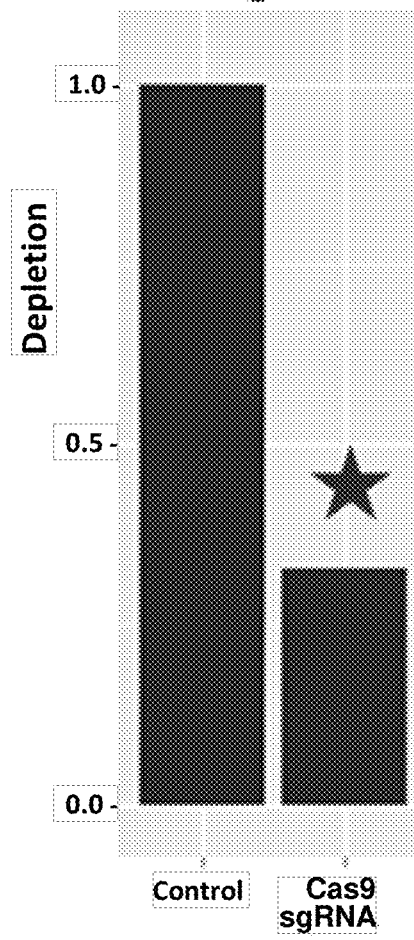
FIG. 7 provides data demonstrating the depletion of a target nucleic acid (18S rRNA in this example) in a nucleic acid library for next generation sequencing using a nucleic acid guided nuclease according to one embodiment of the present disclosure. Panel A shows a bar graph indicating the amount of depletion of a target nucleic using one or two example nucleic acid guided nucleases. Panel B shows the amount of depletion of the target nucleic acid using increasing amounts of a nuclease according to one embodiment of the present disclosure. In this example, a pool of nucleic acid guided nucleases is employed, in which the pool includes a single type of nuclease component and various species of nucleic acid guide components having different nucleotide sequences.
Figure 7:
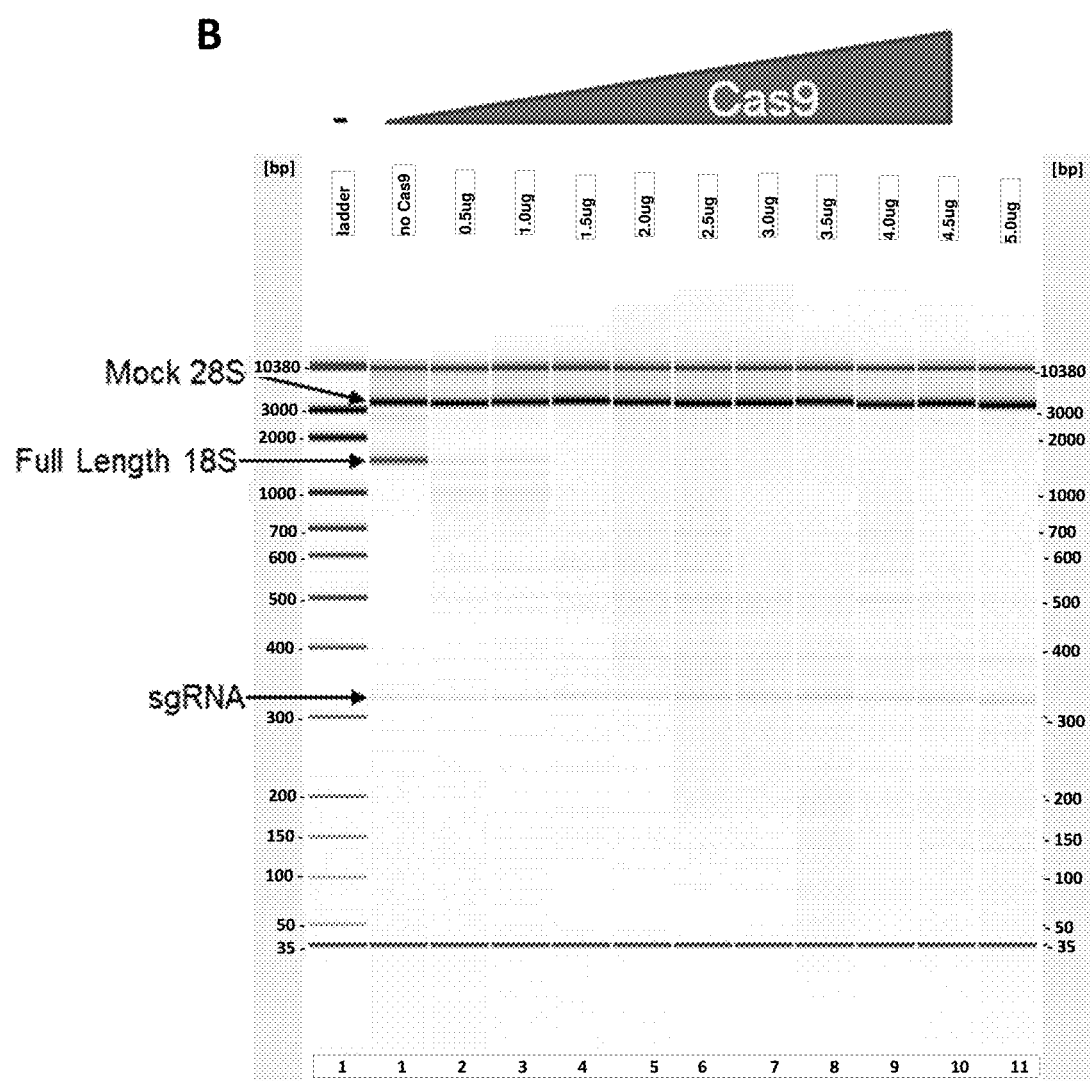

As shown in Panel A of FIG. 7, depletion of the target sequence only occurred in the library treated with both Cas9 and the specific guide RNA.

In a separate experiment, a target cDNA corresponding to 18S rRNA was degraded using a pool of sgRNAs targeting the target cDNA along its length about every 50 bp. The pool was generated by PCR amplifying 35 sgDNA templates (using the approach shown in FIG. 2), and then in vitro transcribing the corresponding 35 sgRNAs in a pooled in vitro transcription reaction. This is one of the key advantages of the method of the present disclosure shown in FIG. 2, as large quantities of a complex collection of different sgRNA sequences can be produced in a single reaction for depleting a single target (by tiling across the target with sgRNAs having different target-specific sequences) or depleting multiple targets using the collection of sgRNAs.

In this experiment, a model target was used that included a target corresponding to the full-length 18S RNA (25 ng) and 55 ng of a 5800 bp plasmid iPCR product (used as a surrogate for the 28S rRNA). This ratio approximates the ratio (in mass) of 18S and 28S rRNA in a 20 nM RNA-Seq library with no depletion. As shown in Panel B of FIG. 7, the 18S fragment was thoroughly depleted/degraded by treatment with the sgRNA pool, while the iPCR fragment was unaffected. Depletion of the target nucleic acid results in failure of the target to cluster on the sequencer (e.g., an Illumina® sequencer) because, at most, the target only has a sequencing adapter at one of its ends following cleavage. Alternatively, the depleted target fragments are sufficiently small that they are lost following purification (e.g., SPRI bead purification) and thus not available for sequencing.

Figure 8:
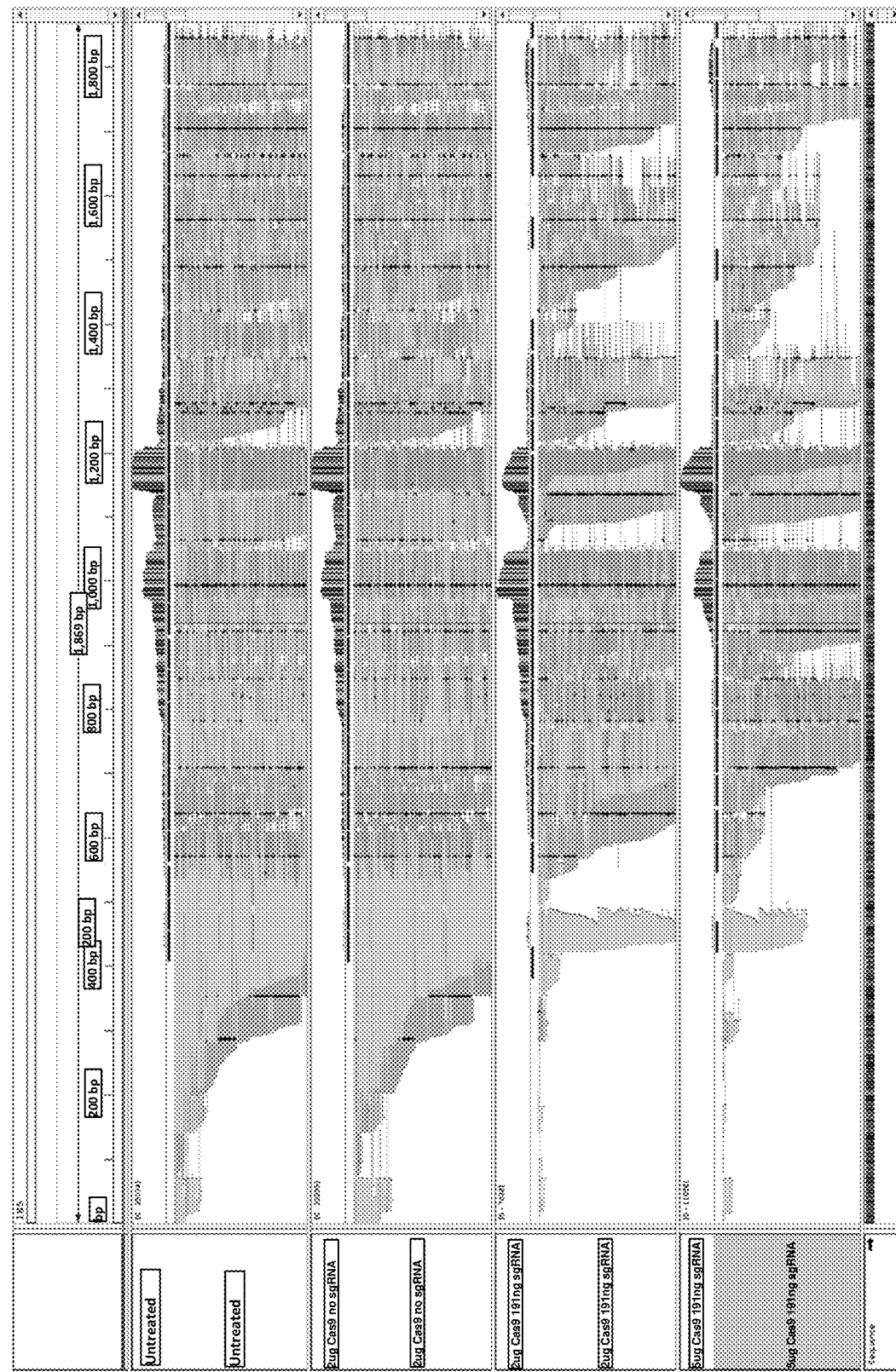
FIG. 8 provides data demonstrating the depletion of a target nucleic acid using a nucleic acid guided nuclease according to one embodiment of the present disclosure. In this example, a pool of nucleic acid guided nucleases is employed, in which the pool includes a single type of nuclease component and various species of nucleic acid guide components having different nucleotide sequences.
Figure 9:
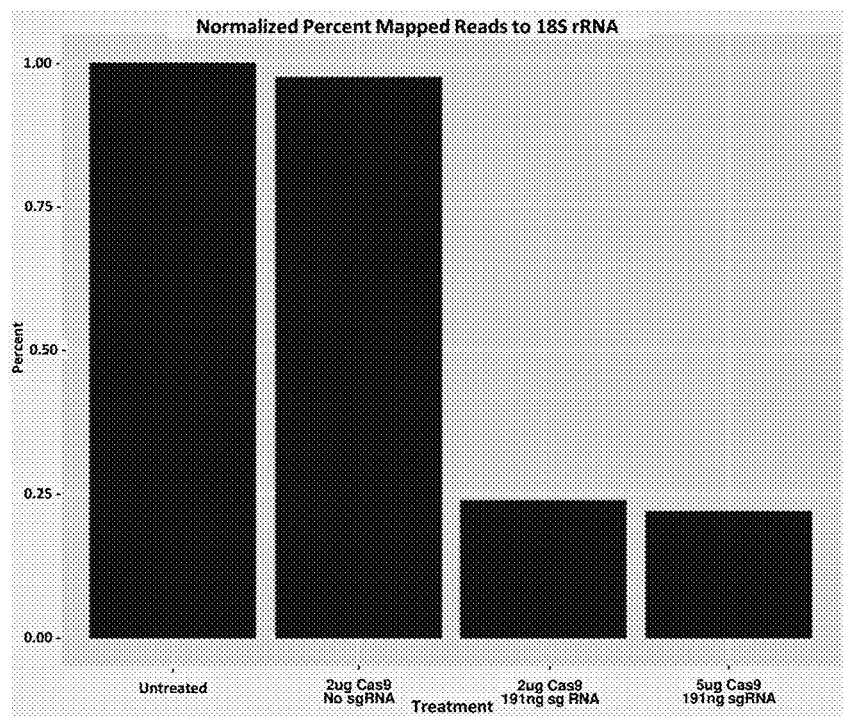
FIG. 9 is a bar graph showing sequencing results and demonstrating the effects of depleting a target nucleic acid from a sequencing library using a method according to one embodiment of the present disclosure.

Example 4: Depletion of 18s rRNA Using a Pool of Nucleic Acid Guided Nucleases In this experiment, sequencing libraries were generated from 100 ng Human Brain Total RNA (Clontech) using the SMARTer Stranded RNA-Seq Kit (Clontech). 70 ng of library was incubated with 0, 2, or 5 µg of recombinantly purified Cas9 and 0 or 191 ng of the 35 sgRNA pool described in the previous experiment in 20 µl 1×NEB3.1 buffer for one hour at 37° C. The Cas9 was then heat inactivated for 10 minutes at 70° C. The libraries were then pooled and sequenced on a MiSeq instrument. The resulting sequences were mapped against the human genome, hg19, and rRNA transcripts simultaneously using the STAR aligner. FIG. 8 illustrates the reduction in sequence coverage of the 18S rRNA transcript resulting only from treatment with both Cas9 and the sgRNA pool. The number of sequencing reads mapped to the 18S rRNA were normalized to the total number of reads sequenced and plotted in FIG. 9, demonstrating an ~75% reduction in sequences mapping to the 18S transcript.

Examples 1-4: Sequence Information

The sgRNA described in examples 1-4 contained the sgRNA scaffold shown in FIG. 1 with the following target-specific sequences: sgRNA1 used in examples 1 and 2:

UUAUCAGAUCAAAACCAACC (SEQ ID NO: 1)

sgRNA2 used in examples 1, 2 and 3:

UAAUCAAGAACGAAAGUCGG (SEQ ID NO: 2)

pool of 35 sgRNA used in examples 3 and 4: (SEQ ID NO:3 to 37)

| | |
|---|---|
| GACAAGCAUAUGCUACUGGC | CGGCGCAAUACGAAUGCCCC |
| CGGUACAGUGAAACUGCGAA | CGCUCGGUCCGUCUUGCGC |
| GGAGAGGAGCGAGCGACCAA | UAAUCAAGAACGAAAGUCGG |
| UAGAGCUAAUACAUGCCGAC | CGGUCGGCAUCGUUUAUGGU |
| UUAUCAGAUCAAAACCAACC | GUUUCCCGGAAGCUGCCCGG |
| GGGGCGGGCGCCGGCGGCUU | CUGAAACUUAAAGGAAUUGA |
| CGAUCGCACGCCCCCCGUGG | GGCUUAAUUUGACUCAACAC |
| GGUAGUCGCCGUGCCUACCA | CUGUCAAUCCUGUCCGUGUC |
| UCAGGGUUCGAUUCCGGAGA | GCAUGGCCGUUCUUAGUUGG |
| UGCGCGCCUGCUGCCUUCCU | GCCAGAGUCUCGUUCGUUAU |
| AACAAUACAGGACUCUUUCG | GCGUCCCCAACUUCUUAGA |
| CCUCGUUAAAGGAUUUAAAG | UGUUAUUGCUCAAUCUCGGG |
| UAUUGGAGCUGGAAUUACCG | AGCGUGUGCCUACCCUACGC |
| AAAGCUCGUAGUUGGAUCUU | CCGUUGAACCCCAUUCGUGA |
| CAAGGGGCGGGGACGGGCGG | UACUGGGAAUUCCUCGUUCA |
| UCUUAGCUGAGUGUCCCGCG | GGCGGUGUGUACAAAGGGCA |
| CAAAGCAGGCCCGAGCCGCC | GGCCCUCGGAUCGGCCCCGC |
| GGACCGCGGUUCUAUUUUGU | |

Example 5: Depletion of Target Nucleic Acids by Argonaute (Ago)

Figure 10:
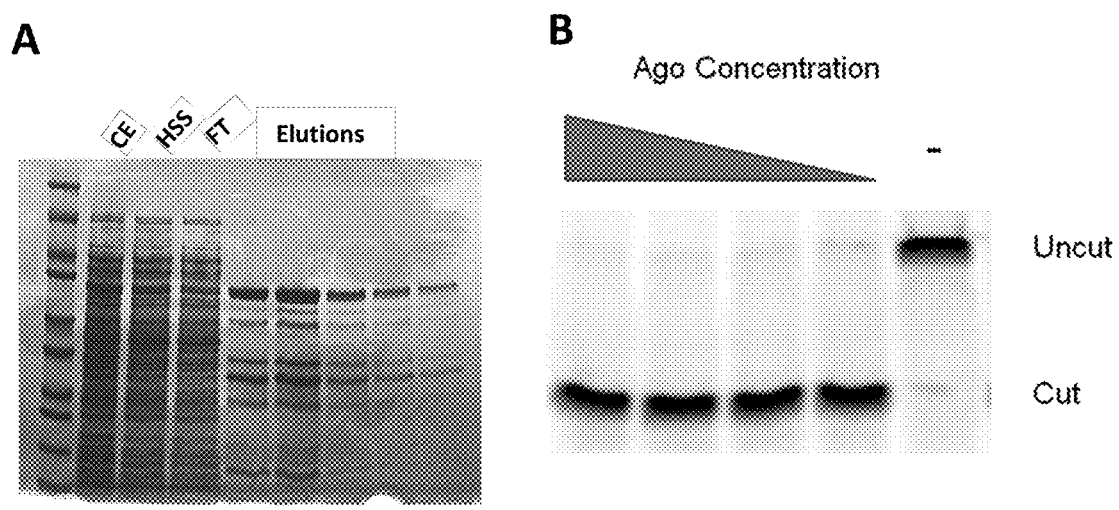
FIG. 10 provides data demonstrating the cleavage of a target nucleic acid using a nucleic acid guided nuclease according to one embodiment of the present disclosure. Panel A shows a gel image demonstrating the purification of an example nuclease component according to one embodiment of the present disclosure. Panel B shows a gel image demonstrating the cleavage of a target nucleic acid using a nucleic acid guided nuclease that includes the nuclease component shown in Panel A.
Figure 11:
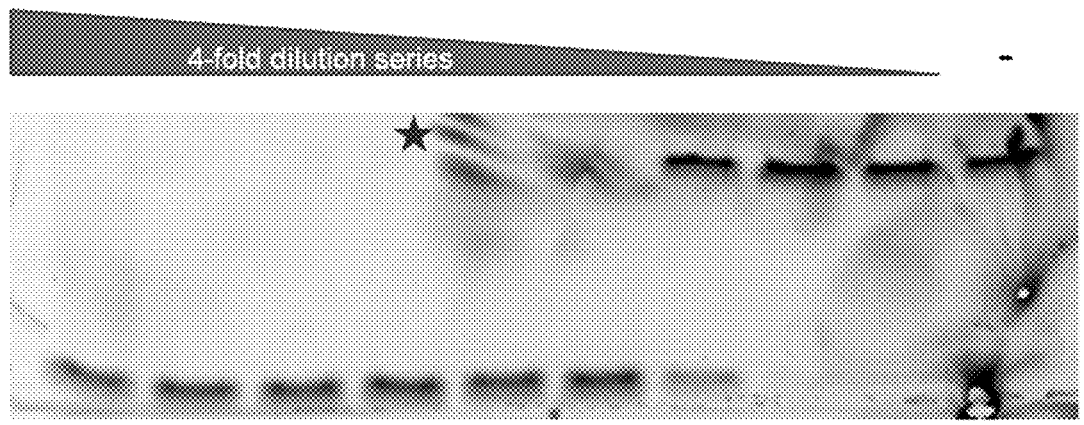
FIG. 11 shows a gel image demonstrating cleavage of a target nucleic acid using various amounts of a nucleic acid guided nuclease according to one embodiment of the present disclosure.

In this example, the ability of the Argonaute (Ago) protein to deplete a target nucleic acid was assessed. His-tagged Tth Ago was expressed and purified (FIG. 10, Panel A). Depletion of a 5' FAM labelled ssDNA representative target was carried out by combining the 500 nM single-stranded DNA, Tth Ago, and 100 nM 5' phosphorylated targeting oligonucleotide complementary to the target single-stranded DNA and incubated at 75° C. for one hour. As shown in FIG. 10, Panel B, the single stranded target was not cleaved in the absence of Ago (far right lane), but was cleaved in the presence of Ago and the targeting oligonucleotide at various Ago concentrations. FIG. 11 demonstrates a similar experiment, but with 20 nM ssDNA target and 50 nM guide DNA to be representative of depleting common library concentrations.

In Example 5, the guide DNA oligo was:

/5'Phos/TGAGGTAGTAGGTTGTATAGT; (SEQ ID NO: 38)
and the targeting oligo was:

/5'6-FAM/AGGTGATAAGACTATACAACCTACTACCTCGAATGTCCGT (SEQ ID NO: 39)

Example 6: Depletion of Target Nucleic Acids from a Collection by Argonaute (Ago)

As demonstrated in Example 5, Argonaute is capable of depleting target ssDNA molecules in solution. If the desired target is double stranded, the double stranded material may be converted to single strands by denaturation, such as with heat or high pH, or by degrading the non-target strand by exonuclease treatment. For example, the mixture may be amplified by a common pair of PCR primers, only one of which is 5' phosphorylated. The amplified product could then be treated with A-exonuclease to yield a ssDNA product. This ssDNA product could then be used as a substrate for cleavage by Ago and a targeting oligonucleotide.

Example 7: Recovery of Targeted Sequences

Figure 12:
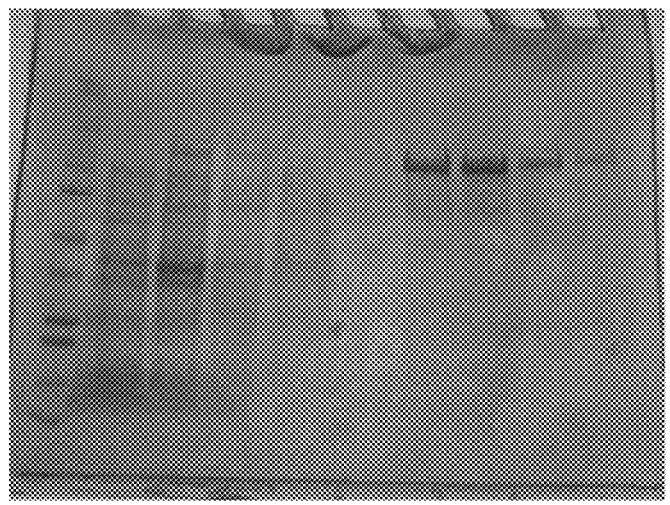
FIG. 12 provides data demonstrating the expression and purification of a 6×HN tagged a10A/H840A mutant of Cas9 (Panel A), and proof-of-principle of the use of the mutant in combination with a pool of nucleic acid guide components to remove target nucleic acids from an initial collection of nucleic acids and produce a nucleic acid sample enriched for the target nucleic acids (Panel B).
Figure 12:
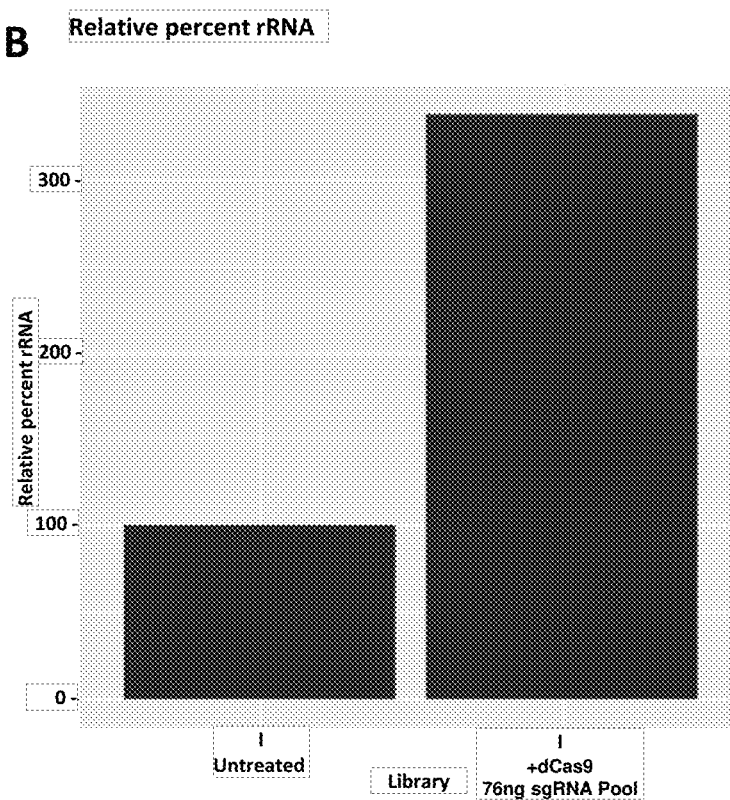

In this Example the 6×HN tagged D10A/H840A mutant of Cas9 (referred to herein as dCas9), was expressed and purified in *E. coli* (FIG. 12, Panel A). RNA-Seq libraries were generated from 100 ng Human Brain PolyA-plus RNA (Clontech) and the SMARTer Stranded RNA-Seq kit (Clontech). 10 ng of library was combined with ~1.25 µg dCas9 and 76 ng of a pool of 190 sgRNA designed every ~50 bp on the human 5S, 5.8S, 18S, 28S, mt12S, and mt16S sequences in 10 µl 1×NEB3.1. The mixture was incubated at 37° C. for one hour. Then 10 µg of salmon sperm DNA (Life Technologies) was added and the reaction was allowed to proceed for an additional 30 minutes at 37° C. 5 µl of TALON magnetic beads (Clontech) equilibrated in 10 µl NEB3 was added to the tubes and incubated at 25° C. with rotation for 30 minutes. The beads were washed twice with 200 µl NEB. 50 µl of SeqAmp PCR Mastermix (1×SeqAmp Buffer, 1 µl SeqAmp DNA polymerase, and 250 nM Illumina P5 and P7 PCR primers) was added to the washed beads and amplified with 15 cycles of PCR (94° C. 1 minute, 15×(98° C.-15s, 55° C.-15s, 68° C.-30s)). The amplified product was purified with 50 µl AMPure beads (Beckman) according to the manufacturer's instructions and eluted in 20 µl 10 mM Tris-HCl pH8.5 0.1% Tween-20. The library was then sequenced on a MiSeq instrument. The resulting sequences were mapped against the human genome, hg19, and rRNA transcripts simultaneously using the STAR aligner. Reads mapping to rRNA were identified by Picard RNA-Seq Metrics, and the relative amounts of sequences mapping to rRNA are plotted in FIG. 12, Panel B, showing a ~340% enrichment verses an untreated library. This example demonstrates that nucleic acid guided nucleases may be used to deplete target nucleic acids by removal of the target nucleic acids from an initial collection of nucleic acids, for subsequent recovery and production of a sample enriched for the target nucleic acids.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of selectively separating one or more target nucleic acids from a composition, the method comprising:
obtaining a composition comprising both target nucleic acids and non-target nucleic acids;
contacting the composition with one or more cleavage-deficient nucleases that lack nuclease activity and one or more guide nucleic acids that guide the one or more cleavage-deficient nucleases to the one or more target nucleic acids to produce a contacted composition, wherein the contacted composition comprises the target nucleic acids, the non-target nucleic acids, the one or more cleavage-deficient nucleases, and the one or more guide nucleic acids, and the one or more cleavage-deficient nucleases, the one or more guide nucleic acids, and the one or more target nucleic acids form a complex in which the one or more guide nucleic acids specifically hybridize with the one or more target nucleic acids; and separating the complex from the contacted composition, thereby selectively separating the one or more target nucleic acids from the composition.

2. The method according to claim 1, wherein the one or more target nucleic acids are double-stranded nucleic acids.

3. The method according to claim 1, wherein the one or more target nucleic acids are selected from the group consisting of cDNA, DNA, RNA, and any combination of thereof.

4. The method according to claim 3, wherein the one or more target nucleic acids are cDNA.

5. The method according to claim 4, wherein the cDNA is transcribed from ribosomal RNAs or mRNA.

6. The method according to claim 1, wherein the one or more guide nucleic acids are RNA.

7. The method of claim 6, wherein the RNA is single strand-guide RNA specifically hybridizing with at least one human rRNAs selected from the group consisting of 5S, 5.8S, 18S, and 28S rRNAs.

8. The method according to claim 1, wherein the one or more guide nucleic acids is DNA.

9. The method according to claim 1, wherein the one or more cleavage-deficient nucleases are selected from the group consisting of a Cas nuclease, an Argonaute nuclease, and a combination of thereof.

10. The method according to claim 9, wherein the one or more cleavage-deficient nucleases are a Cas nuclease.

11. The method according to claim 1, wherein the one or more cleavage-deficient nucleases comprise a tag, and the complex is separated from the composition by immobilizing the complex to the surface of a solid phase including a binding partner that binds to the tag.

12. The method according to claim 11, wherein the tag is an epitope tag, FLAG tag, HA tag, His tag, Myc tag, S-tag, SBP tag, Softag, GST tag, GFP tag, biotin, streptavidin, or 6-His tag.

13. A method of producing a composition selectively enriched for one or more target nucleic acids, the method comprising:

obtaining a composition comprising both target nucleic acids and non-target nucleic acids;

contacting the composition with one or more cleavage-deficient nucleases that lack nuclease activity and one or more guide nucleic acids that guide the cleavage-deficient nucleases to the one or more target nucleic acids to produce a contacted composition, wherein the contacted composition comprises the target nucleic acids, the non-target nucleic acids, the one or more cleavage-deficient nucleases, and the one or more guide nucleic acids, and the one or more guide nucleic acids specifically hybridize with the one or more target nucleic acids to form a complex; and separating the complex from the contacted composition, thereby producing a composition selectively enriched with the one or more target nucleic acids.

14. The method according to claim 13, wherein the one or more target nucleic acids are double-stranded nucleic acids.

15. The method according to claim 13, wherein the one or more target nucleic acids are selected from the group consisting of cDNA, DNA, RNA, and any combination of thereof.

16. The method according to claim 13, wherein the one or more guide nucleic acids are RNA.

17. The method of claim 16, wherein the RNA is single strand-guide RNA specifically hybridizing with at least one human rRNAs selected from the group consisting of 5S, 5.8S, 18S, and 28S rRNAs.

18. The method according to claim 13, wherein the one or more cleavage-deficient nucleases are selected from the group of consisting of a Cas nuclease, an Argonaute nuclease, and a combination of thereof.

19. The method according to claim 13, wherein the one or more cleavage-deficient nucleases comprise a tag, and the complex is separated from the composition by immobilizing the complex to the surface of a solid phase including a binding partner that binds to the tag.

20. The method according to claim 19, wherein the tag is an epitope tag, FLAG tag, HA tag, His tag, Myc tag, S-tag, SBP tag, Softag, GST tag, GFP tag, biotin, streptavidin, or 6-His tag.

* * * * *

UNITED STATES PATENT AND TRADEMARK OFFICE
CERTIFICATE OF CORRECTION

PATENT NO.         : 11,884,963 B2
APPLICATION NO.    : 17/235702
DATED              : January 30, 2024
INVENTOR(S)        : Andrew Alan Farmer et al.

It is certified that error appears in the above-identified patent and that said Letters Patent is hereby corrected as shown below:

In the Specification

Please replace "al 0A/H840A" with -- D10A/H840A -- (Column 3, Line 8).

Please replace "810%," with -- 81%, -- (Column 5, Line 65).

Please replace "840%," with -- 84%, -- (Column 5, Line 65).

Please replace "870%," with -- 87%, -- (Column 5, Line 66).

Please replace "880%," with -- 88%, -- (Column 5, Line 66).

Please replace "U52011/0301073)." with -- US2011/0301073). -- (Column 6, Lines 64-65).

Please replace "Cas1 B," with -- Cas1B, -- (Column 8, Line 4).

Please replace "Glade" with -- clade -- (Column 8, Line 39).

Please replace "Glade." with -- clade. -- (Column 8, Line 40).

Please replace "Birkhäauser" with -- Birkhäuser -- (Column 9, Line 56).

Please replace "0.1 µg/µl" with -- 0.1 pg/µl -- (Column 12, Line 30).

Please replace "50 µm." with -- 50 µM. -- (Column 12, Line 33).

Please replace "HiSeg™ MiSeg™" with -- HiSeq™, MiSeq™ -- (Column 15, Line 24).

Please replace "polyA±blood RNA)." with -- polyA+blood RNA). -- (Column 19, Line 8).

Signed and Sealed this
Second Day of July, 2024

Katherine Kelly Vidal
*Director of the United States Patent and Trademark Office*

CERTIFICATE OF CORRECTION (continued)
U.S. Pat. No. 11,884,963 B2

Please replace "Illumin®—" with -- Illumina®— -- (Column 20, Line 2).

Please replace "(CMB0640" with -- (CMBO640 -- (Column 22, Line 15).

Please replace "CMB0640" with -- CMBO640 -- (Column 22, Line 24).

Please replace "1~4" with -- 1-4 -- (Column 23, Line 55).

Please replace "A-exonuclease" with -- λ-exonuclease -- (Column 25, Line 6).

Please replace "IIlumina" with -- Illumina -- (Column 25, Lines 29-30).